US011518366B2

(12) United States Patent
    Dudar

(10) Patent No.: US 11,518,366 B2
(45) Date of Patent: Dec. 6, 2022

(54) SYSTEMS AND METHODS FOR DIAGNOSING A VEHICLE ENGINE INTAKE MANIFOLD AND EXHAUST SYSTEM

(71) Applicant: Ford Global Technologies, LLC, Dearborn, MI (US)

(72) Inventor: Aed M. Dudar, Canton, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 374 days.

(21) Appl. No.: 16/794,874

(22) Filed: Feb. 19, 2020

(65) Prior Publication Data

US 2020/0180604 A1    Jun. 11, 2020

Related U.S. Application Data

(62) Division of application No. 15/804,359, filed on Nov. 6, 2017, now Pat. No. 10,604,147.

(51) Int. Cl.

| B60W 20/50 | (2016.01) |
| F02D 41/18 | (2006.01) |
| F02D 41/22 | (2006.01) |
| B60W 40/08 | (2012.01) |
| F02M 35/10 | (2006.01) |
| F02N 11/00 | (2006.01) |
| G01M 15/10 | (2006.01) |

(Continued)

(52) U.S. Cl.
CPC ............ *B60W 20/50* (2013.01); *B60W 40/08* (2013.01); *F02D 41/18* (2013.01); *F02D 41/22* (2013.01); *F02M 35/10386* (2013.01); *F02N 11/003* (2013.01); *G01M 15/106* (2013.01); *B60W 2040/0881* (2013.01); *F02D 41/0002* (2013.01); *F02D 41/005* (2013.01); *F02D 41/042* (2013.01); *F02D 2250/24* (2013.01); *G01N 33/0006* (2013.01)

(58) Field of Classification Search
CPC ........... B60W 20/50; B60W 2050/021; B60W 2040/0881; B60W 40/08; Y02T 10/40; F02N 11/0807; F02N 11/003; G01N 33/0006; F02D 2250/24; F02D 41/042; F02D 41/005; F02D 41/0002; F02D 41/22; F02D 41/18; G01M 15/106; F02M 35/10386

See application file for complete search history.

(56) References Cited

U.S. PATENT DOCUMENTS 4,100,902 A * 7/1978 Kosuda ................. F02M 69/02
                                                         123/530
4,205,377 A * 5/1980 Oyama ............... F02D 41/1479
                                                         123/480

(Continued)

*Primary Examiner* — Behrang Badii
(74) *Attorney, Agent, or Firm* — Vincent Mastrogiacomo; McCoy Russell LLP

(57) ABSTRACT

Methods and systems are provided for pinpointing a source of degradation in a vehicle engine system. In one example, a method includes spinning an engine of a vehicle unfueled in a forward and a reverse direction, in no particular order, and recording a first intake air flow and a second intake air flow, respectively, in an intake of the engine, and where the source of degradation is indicated as a function of both the first air flow and the second air flow. In this way, the degradation of the vehicle engine system may be pinpointed as to being located in the intake manifold, the exhaust system, or the engine.

11 Claims, 9 Drawing Sheets

(51) Int. Cl.
*F02D 41/04* (2006.01)
*F02D 41/00* (2006.01)
*G01N 33/00* (2006.01)

(56) References Cited

U.S. PATENT DOCUMENTS

| | | | |
|---|---|---|---|
| 5,564,393 A * | 10/1996 | Asano | F02D 41/047 |
| | | | 123/492 |
| 6,230,695 B1 | 5/2001 | Coleman et al. | |
| 6,516,787 B1 | 2/2003 | Dutart et al. | |
| 6,763,298 B2 | 7/2004 | Boggs et al. | |
| 6,895,934 B2 | 5/2005 | Kirschke et al. | |
| 8,739,766 B2 | 6/2014 | Jentz et al. | |
| 10,436,138 B2 | 10/2019 | Dudar | |
| 2003/0230287 A1 | 12/2003 | Ozeki et al. | |
| 2004/0000135 A1* | 1/2004 | Uchida | F02D 41/1495 |
| | | | 60/285 |
| 2008/0255749 A1 | 10/2008 | Murakami | |
| 2009/0187301 A1 | 7/2009 | Wang et al. | |
| 2014/0233870 A1 | 8/2014 | Ohama | |
| 2014/0238370 A1* | 8/2014 | Pursifull | G01N 33/0006 |
| | | | 123/690 |
| 2016/0332620 A1* | 11/2016 | Dudar | F02M 35/10222 |
| 2017/0356374 A1 | 12/2017 | Rollinger et al. | |
| 2018/0010532 A1 | 1/2018 | Dudar | |
| 2018/0171885 A1 | 6/2018 | Ulrey | |
| 2018/0320611 A1 | 11/2018 | Glugla | |
| 2019/0024599 A1* | 1/2019 | Dudar | F02D 41/1441 |
| 2019/0033170 A1* | 1/2019 | Dudar | G01M 15/106 |

\* cited by examiner

FIG. 8

| | Outcome from engine system diagnostic | Diagnosis |
|---|---|---|
| Ⓐ | MAF ≈ baseline and dP sensor > baseline when engine spun in forward direction <u>and/or</u> MAF ≈ baseline when engine spun in fwd direction but MAF < baseline when engine spun in reverse direction | Degradation stemming from intake manifold |
| Ⓑ | MAF ≈ baseline and dP sensor < baseline when engine spun in forward direction <u>and/or</u> MAF ≈ baseline when engine spun in fwd direction but MAF > baseline when engine spun in reverse direction | Degradation stemming from exhaust system |
| Ⓒ | Both MAF and dP sensor < baseline when engine spun in forward direction <u>and/or</u> MAF < baseline when engine spun in forward direction and reverse direction | Degradation stemming from engine and/or engine mechanical issues |
| Ⓓ | MAF ≈ baseline dP sensor ≈ baseline when engine spun in forward direction <u>and/or</u> MAF ≈ baseline when engine spun in forward direction and reverse direction | Absence of degradation stemming from intake manifold, engine, and exhaust system |

SYSTEMS AND METHODS FOR DIAGNOSING A VEHICLE ENGINE INTAKE MANIFOLD AND EXHAUST SYSTEM

CROSS REFERENCE TO RELATED APPLICATION

The present application is a divisional of U.S. Non-Provisional patent application Ser. No. 15/804,359, entitled "SYSTEMS AND METHODS FOR DIAGNOSING A VEHICLE ENGINE INTAKE MANIFOLD AND EXHAUST SYSTEM," and filed on Nov. 6, 2017. The entire contents of the above-listed application is hereby incorporated by reference for all purposes.

FIELD

The present description relates generally to methods and systems for assessing the presence or absence of degradation in a vehicle engine, engine intake manifold, or engine exhaust system.

BACKGROUND/SUMMARY

Internal combustion engines combust a mixture of fuel and air in order to produce torque to propel a vehicle. Specifically, air is drawn into the engine via an engine intake based on a position of a throttle, and then the air is mixed with fuel. The air-fuel mixture is combusted within engine cylinder(s), to drive piston(s) within the cylinder(s), thus rotating an engine crankshaft. By-products of combustion within the engine cylinders are routed to one or more catalysts via an exhaust manifold, prior to exiting to atmosphere.

Both the engine intake and exhaust systems may exhibit degradation, over time. Any presence of degradation in the intake manifold, exhaust system, or engine may lead to a decrease in fuel economy, and in some examples may lead to an increase in undesired emissions. The inventors have herein recognized these issues.

Engine operation may be regulated based on a number of parameters, such as the air flow rate provided to the engine. A measurement of air flow provided to the engine may be determined by a mass air flow (MAF) sensor, for example. However, in the intake manifold, any presence of degradation downstream of the MAF sensor may result in unmetered air being provided to the engine. As a result, the air-fuel ratio may switch lean. However, there are many other root causes for an engine running lean, such as undesired combustion, exhaust gas oxygen sensors that are not functioning as desired, valve timing issues, the MAF sensor not functioning as desired, etc. Thus, it can be challenging to specifically diagnose the presence or absence of degradation stemming from an intake system or intake manifold downstream of a MAF sensor. Similarly, degradation in the exhaust system may be difficult to pinpoint, if said degradation is downstream of an exhaust gas oxygen sensor, for example.

U.S. Patent No. US20090187301 teaches a method of diagnosing the presence or absence of degradation in an intake manifold of an engine, by comparing manifold absolute pressure to atmospheric pressure. In one example, a significant amount of degradation is indicated responsive to manifold absolute pressure being substantially equivalent to atmospheric pressure.

However, the inventors herein have recognized potential issues with such a method. For example, such a method is unable to diagnose the presence or absence of degradation in an exhaust system of the vehicle. Thus, the inventors have herein developed systems and methods to address such issues. In one example, a method is provided, comprising spinning an engine of a vehicle unfueled in a forward and a reverse direction to obtain a first intake air flow and a second intake air flow, respectively, in an intake of the engine; and indicating a source of degradation stemming from one of the engine, an intake manifold of the engine, or an exhaust system of the engine based on both the first air flow and the second air flow.

In one example, prior to spinning the engine unfueled in the forward and the reverse direction to obtain the first intake air flow and the second intake air flow, obtaining a set of baseline comparator data that includes spinning the engine unfueled in the forward and the reverse direction to obtain a first baseline intake air flow and a second baseline intake air flow; and wherein spinning the engine unfueled in the forward and the reverse direction is conducted via a motor powered by a battery.

In this way, degradation stemming from one of the engine, intake manifold of the engine, or exhaust system of the engine, may be diagnosed, based on one test diagnostic procedure. By pinpointing where in an engine system there is degradation, repairs may be streamlined, customer satisfaction may be improved, and release of undesired emissions to atmosphere may be reduced.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIG. 8 shows an example lookup table that may be used to interpret results of the method of FIG. 6.

DETAILED DESCRIPTION

Figure 2:
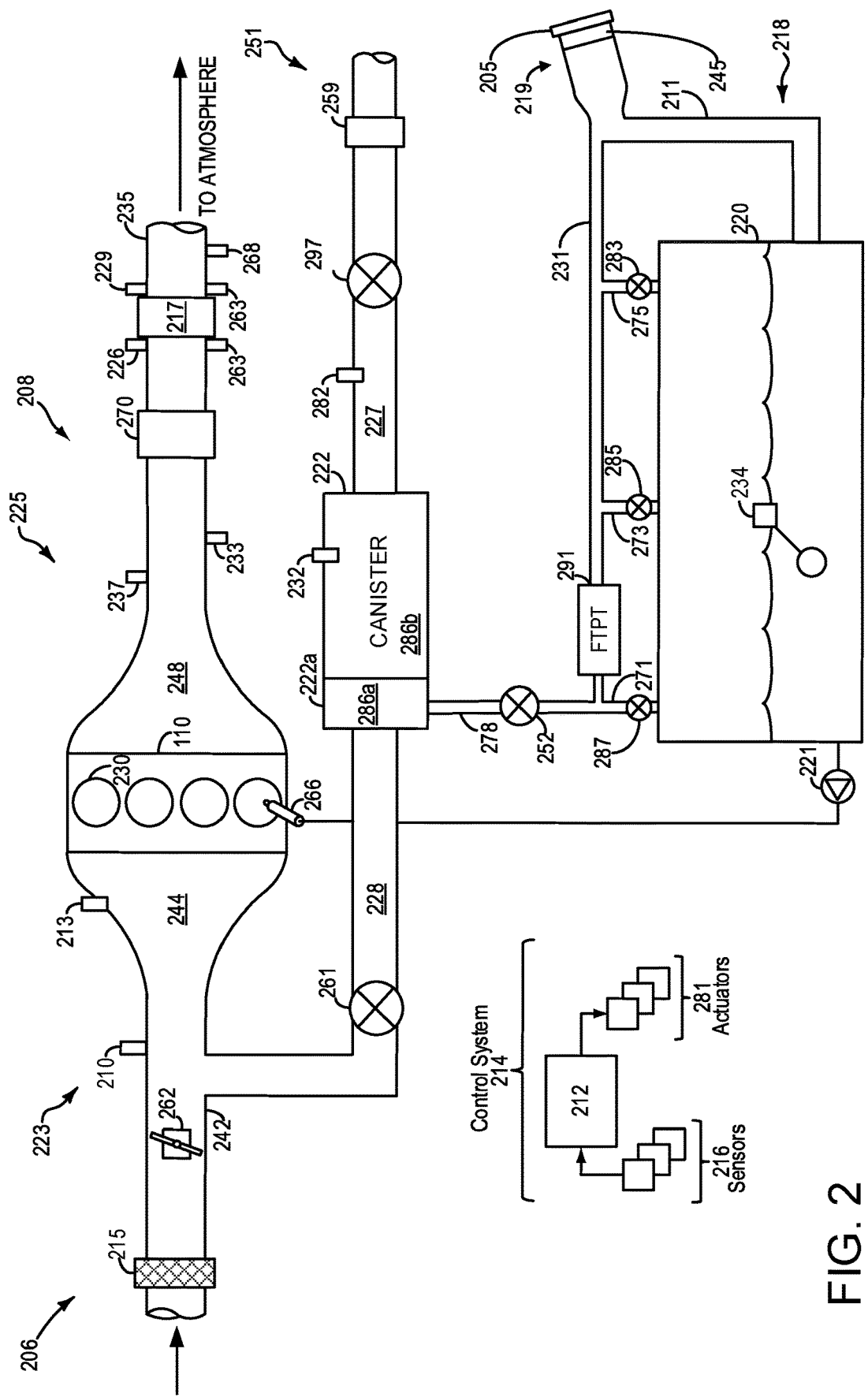
FIG. 2 schematically shows an example vehicle system with a fuel system and an evaporative emissions system.
Figure 3A:
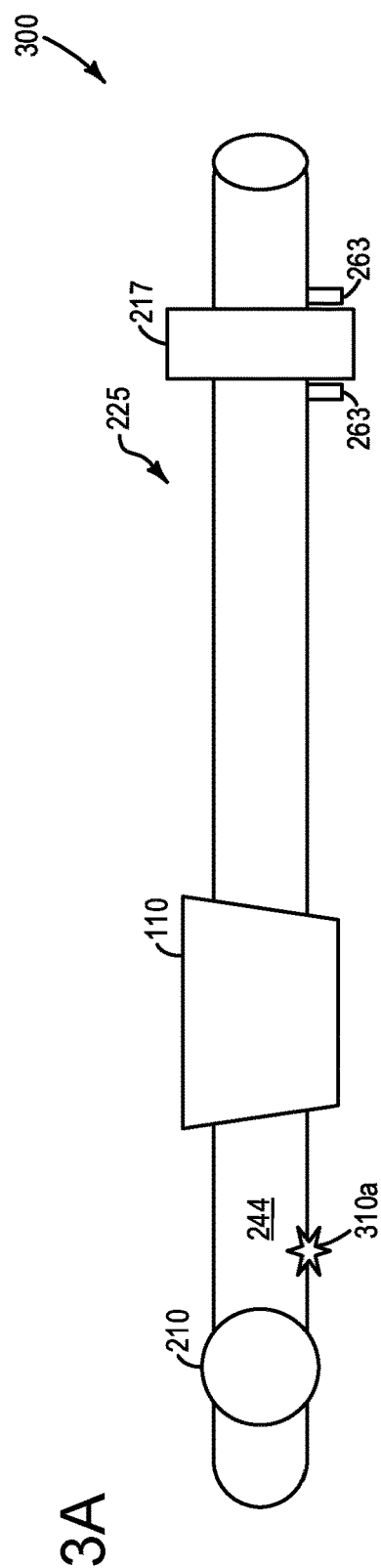
FIGS. 3A-3C schematically illustrate block diagrams of a vehicle intake and exhaust system of an engine, with potential locations for degradation illustrated.
Figure 3B:
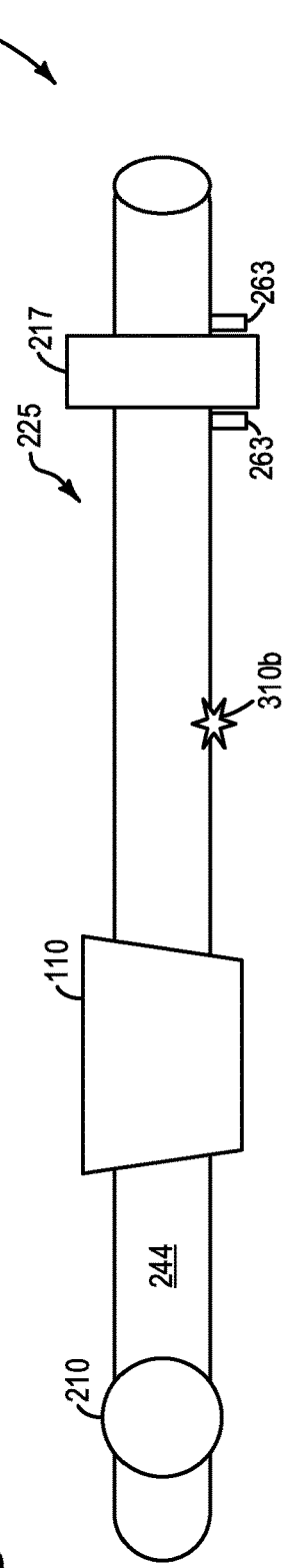
Figure 3C:
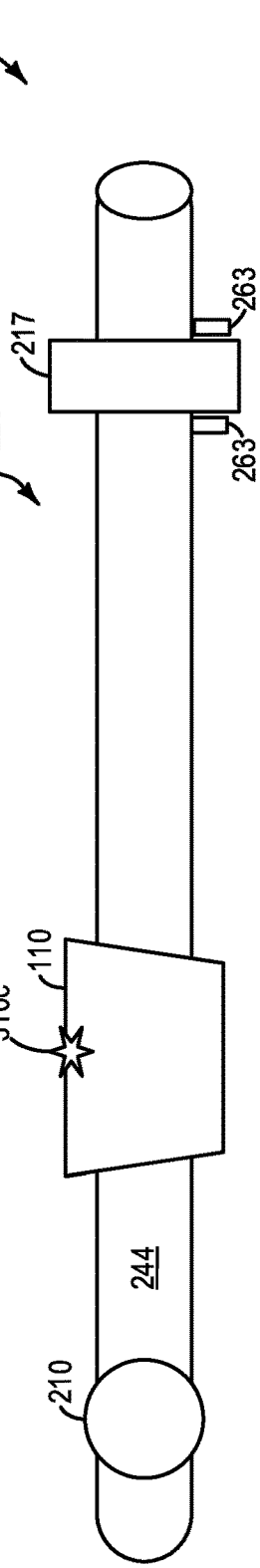
Figure 4:
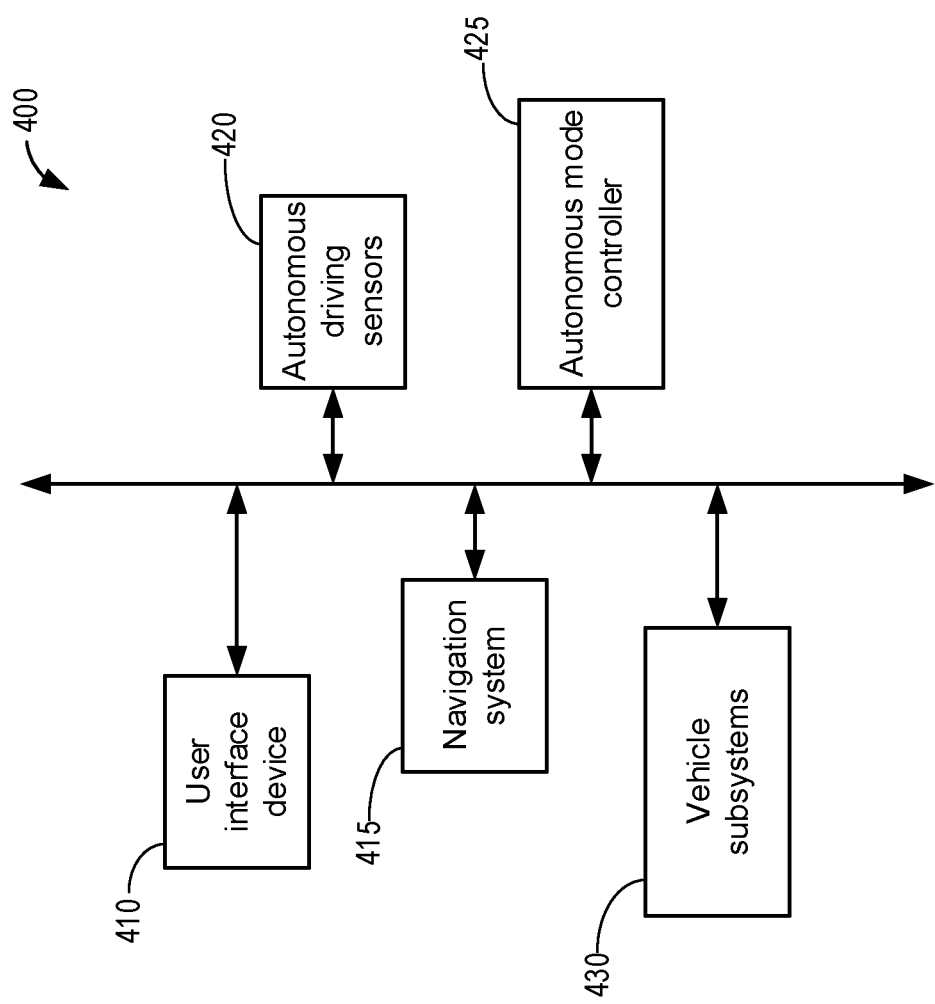
FIG. 4 schematically illustrates a block diagram of an example autonomous driving system.
Figure 6:
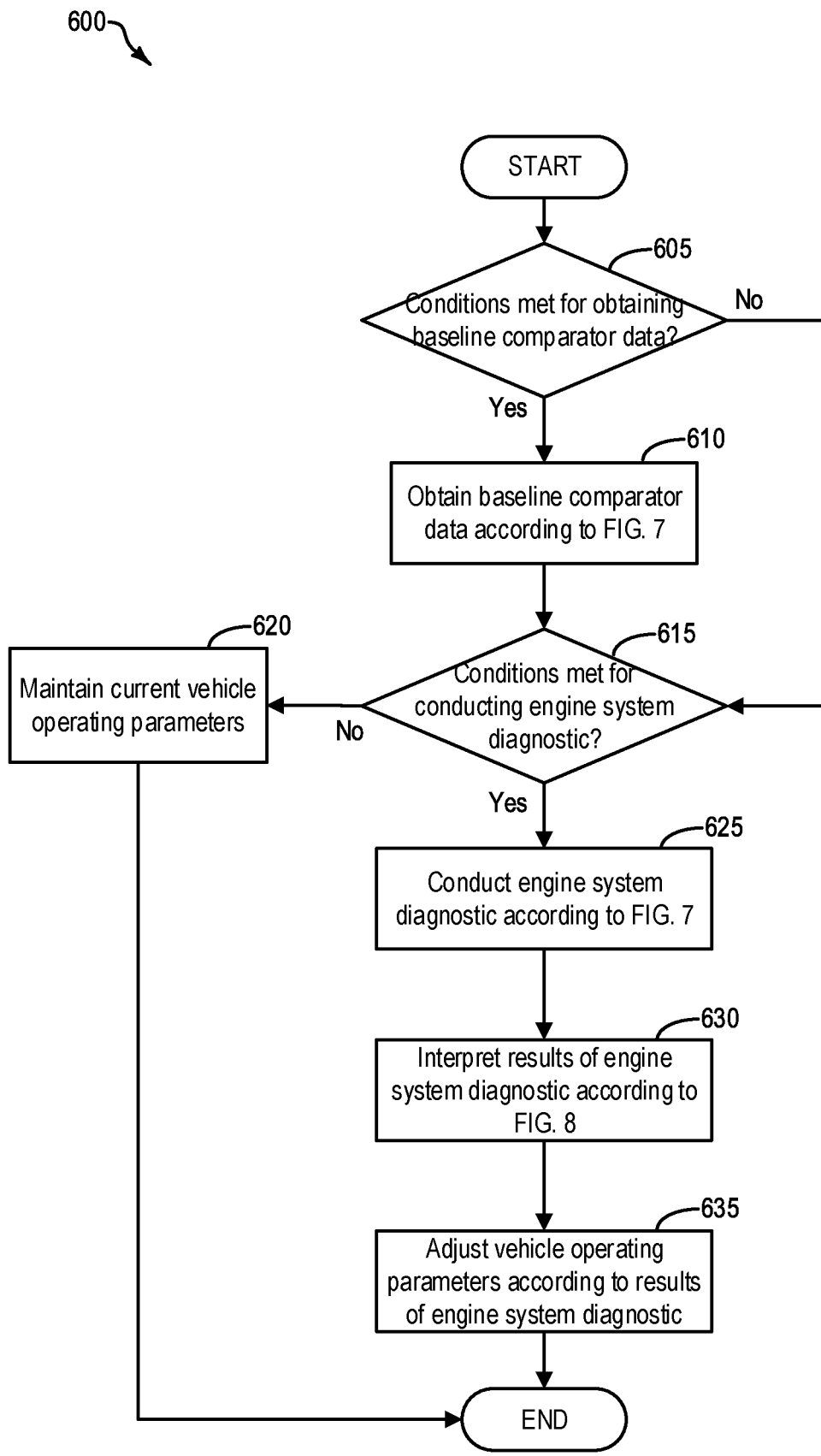
FIG. 6 shows a high level flowchart for indicating a presence or absence of degradation stemming from an intake manifold, exhaust system, or an engine.
Figure 7:
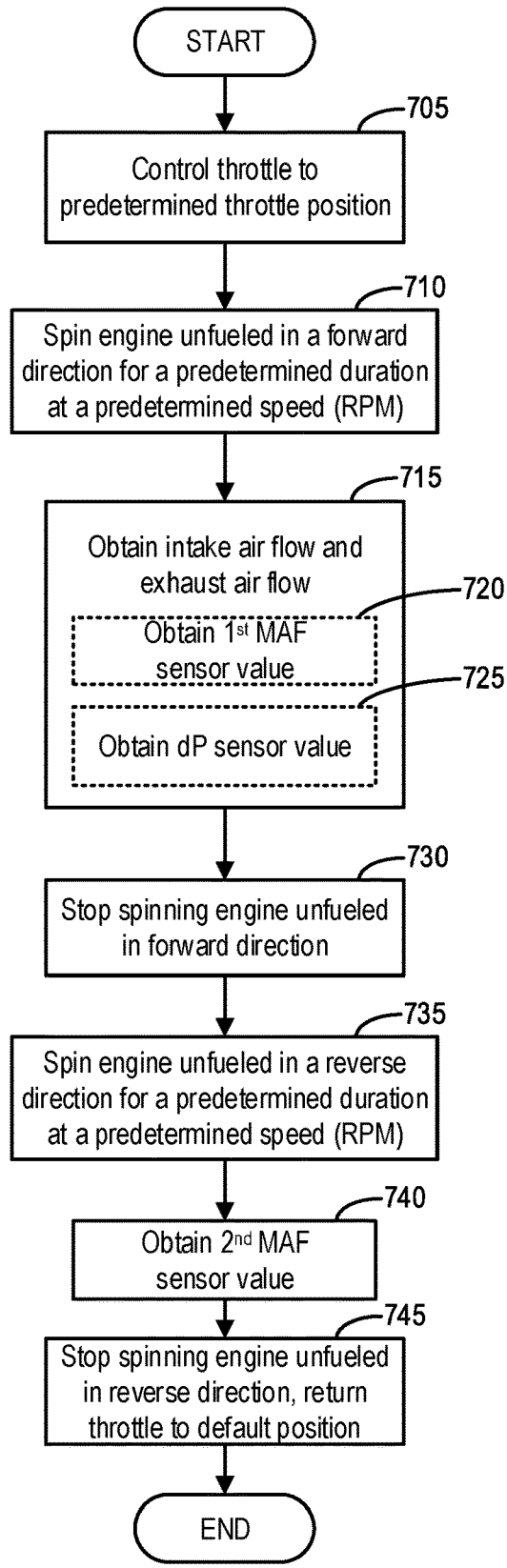
FIG. 7 shows a high level flowchart detailing steps for obtaining baseline comparator data and for conducting an engine system diagnostic, for use in the method of FIG. 6 above.
Figure 9:
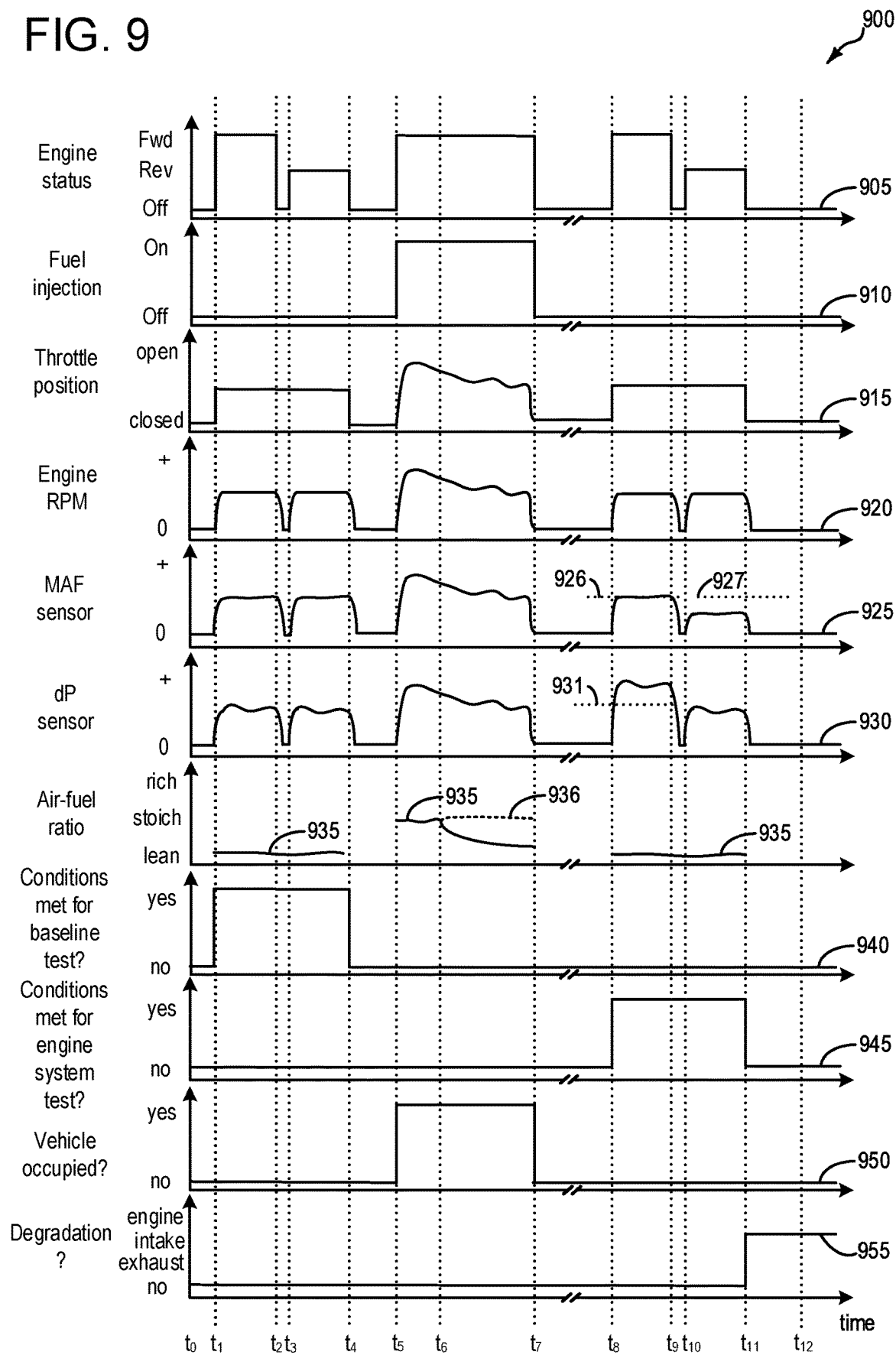
FIG. 9 shows an example timeline for conducting an engine system diagnostic, according to the methods of FIG. 6 and FIG. 7.

The following description relates to systems and methods for pinpointing sources of degradation stemming from either an intake manifold, exhaust system, or an engine of a vehicle. Such systems and methods may include spinning or rotating an engine without fuel injection, in a forward (or default) direction and then a reverse direction, where spinning the engine unfueled is conducted via an electric motor of a hybrid vehicle, such as the hybrid vehicle depicted at FIG. 1. More specifically, to diagnose a source of degradation in an engine system (the engine system including the engine intake manifold, engine exhaust system, and engine), air flow in an intake system of the vehicle, and air flow in the exhaust system may be monitored under a set of predetermined conditions, and compared to a set of baseline air flow in the intake system and baseline air flow in the exhaust system measured under a substantially equivalent set of predetermined conditions. Measuring air flow in the intake system may be conducted via a mass air flow (MAF) sensor positioned in the intake system, where air flow in the intake system may be measured under conditions where the engine is spun in the forward direction and the reverse direction. Measuring air flow in the exhaust system may be conducted via a gasoline particulate filter (GPF) differential pressure sensor under conditions where the engine is spun in the forward direction, where the GPF differential pressure sensor is positioned in the exhaust system downstream of an exhaust manifold, as illustrated in FIG. 2. By comparing air flow in the intake system and air flow in the exhaust system to baseline measurements conducted under conditions where degradation is not present in the engine system, sources of degradation may be pinpointed as to stemming from the intake manifold, exhaust system, or engine, as illustrated at FIGS. 3A-3C. In some examples, the set of predetermined conditions for conducting baseline air flow measurements on the intake system and exhaust system, and test air flow measurements on the intake system and exhaust system, may comprise an indication that the vehicle is not occupied. Thus, such measurements may in some examples be carried out in an autonomous vehicle that is not occupied, where FIG. 4 depicts an example autonomous vehicle control system. For spinning the engine unfueled in the forward and reverse directions, an H-bridge circuit may be utilized, such as the H-bridge circuit depicted at FIGS. 5A-5B. A method for pinpointing a source of degradation in an intake manifold, exhaust system, or engine is illustrated at FIG. 6. As discussed, such a method may include baseline measurements of air flow in the intake system (under both forward and reverse spinning of the engine) and air flow in the exhaust system (under forward spinning of the engine), in addition to similar measurements during test conditions. Accordingly, a method for obtaining such measurements, for use in the method depicted at FIG. 6, is illustrated at FIG. 7. To interpret the results of such a diagnostic test, the results may be analyzed via a lookup table, such as the lookup table depicted above at FIG. 8. An example timeline for conducting such an engine system test diagnostic procedure is illustrated at FIG. 9.

Figure 1:
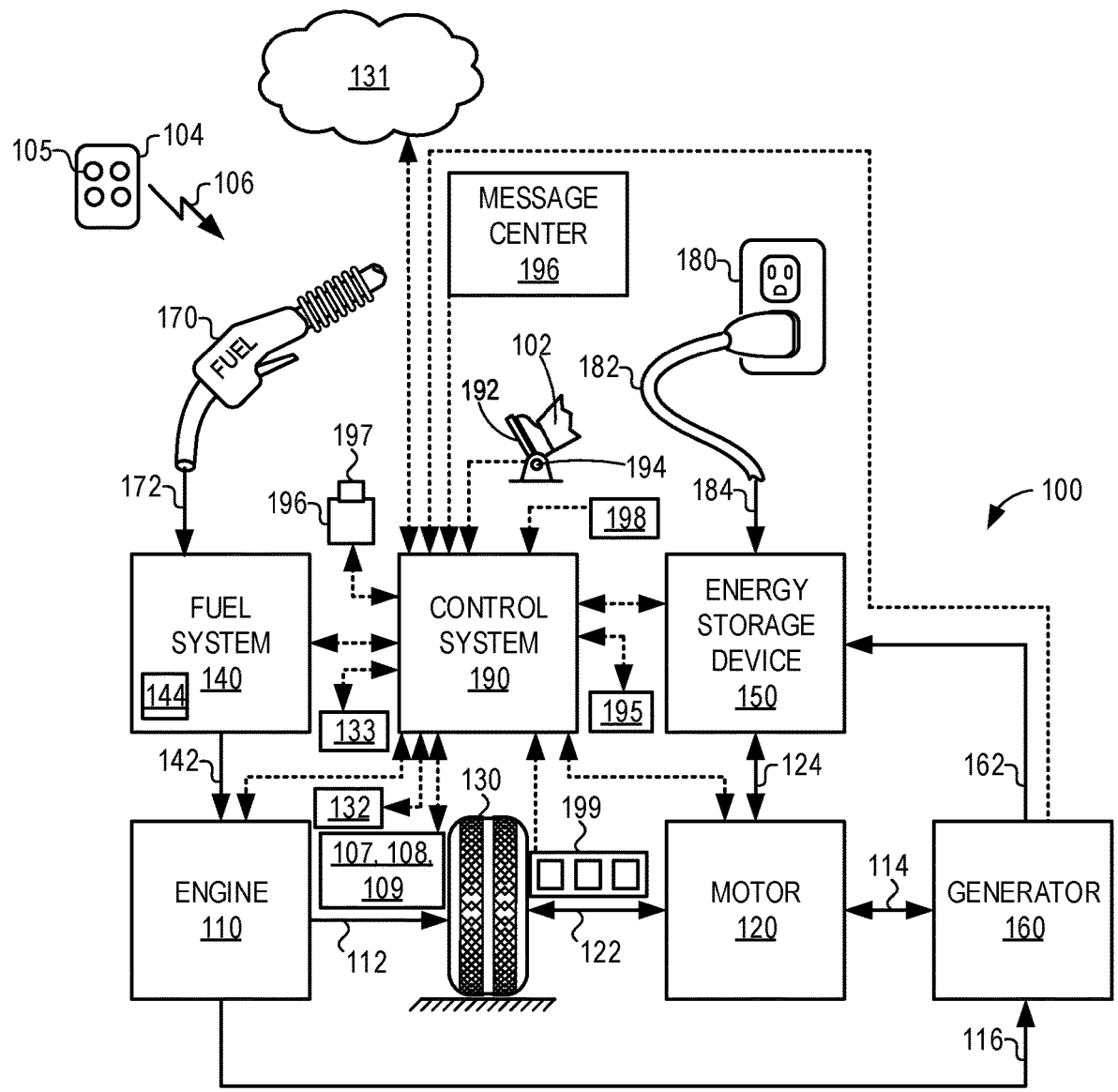
FIG. 1 schematically shows an example vehicle propulsion system.

FIG. 1 illustrates an example vehicle propulsion system 100. Vehicle propulsion system 100 includes a fuel burning engine 110 and a motor 120. As a non-limiting example, engine 110 comprises an internal combustion engine and motor 120 comprises an electric motor. Motor 120 may be configured to utilize or consume a different energy source than engine 110. For example, engine 110 may consume a liquid fuel (e.g., gasoline) to produce an engine output while motor 120 may consume electrical energy to produce a motor output. As such, a vehicle with propulsion system 100 may be referred to as a hybrid electric vehicle (HEV).

Vehicle propulsion system 100 may utilize a variety of different operational modes depending on operating conditions encountered by the vehicle propulsion system. Some of these modes may enable engine 110 to be maintained in an off state (i.e., set to a deactivated state) where combustion of fuel at the engine is discontinued. For example, under select operating conditions, motor 120 may propel the vehicle via drive wheel 130 as indicated by arrow 122 while engine 110 is deactivated.

During other operating conditions, engine 110 may be set to a deactivated state (as described above) while motor 120 may be operated to charge energy storage device 150. For example, motor 120 may receive wheel torque from drive wheel 130 as indicated by arrow 122 where the motor may convert the kinetic energy of the vehicle to electrical energy for storage at energy storage device 150 as indicated by arrow 124. This operation may be referred to as regenerative braking of the vehicle. Thus, motor 120 can provide a generator function in some examples. However, in other examples, generator 160 may instead receive wheel torque from drive wheel 130, where the generator may convert the kinetic energy of the vehicle to electrical energy for storage at energy storage device 150 as indicated by arrow 162.

During still other operating conditions, engine 110 may be operated by combusting fuel received from fuel system 140 as indicated by arrow 142. For example, engine 110 may be operated to propel the vehicle via drive wheel 130 as indicated by arrow 112 while motor 120 is deactivated. During other operating conditions, both engine 110 and motor 120 may each be operated to propel the vehicle via drive wheel 130 as indicated by arrows 112 and 122, respectively. A configuration where both the engine and the motor may selectively propel the vehicle may be referred to as a parallel type vehicle propulsion system. Note that in some examples, motor 120 may propel the vehicle via a first set of drive wheels and engine 110 may propel the vehicle via a second set of drive wheels.

In other examples, vehicle propulsion system 100 may be configured as a series type vehicle propulsion system, whereby the engine does not directly propel the drive wheels. Rather, engine 110 may be operated to power motor 120, which may in turn propel the vehicle via drive wheel 130 as indicated by arrow 122. For example, during select operating conditions, engine 110 may drive generator 160 as indicated by arrow 116, which may in turn supply electrical energy to one or more of motor 120 as indicated by arrow 114 or energy storage device 150 as indicated by arrow 162. As another example, engine 110 may be operated to drive motor 120 which may in turn provide a generator function to convert the engine output to electrical energy, where the electrical energy may be stored at energy storage device 150 for later use by the motor.

In still other examples, which will be discussed in detail below, motor 120 may in some examples be utilized to spin or rotate the motor in an unfueled configuration. More specifically, motor 120 may rotate the engine unfueled, using power from onboard energy storage device 150, which may include a battery, capacitor, super-capacitor, etc., for example. In a case where motor 120 is used to rotate the engine unfueled, fuel injection to engine cylinders may be prevented, and spark may not be provided to each of the engine cylinders. As will be discussed in further detail below, the engine may in some examples be spun or rotated unfueled, in a forward or default direction, whereas in other examples, the engine may be spun or rotated unfueled in a reverse direction. For example, an H-bridge circuit (see FIGS. 5A-5B) may be utilized to spin the engine in a forward or reverse direction.

Fuel system 140 may include one or more fuel storage tanks 144 for storing fuel on-board the vehicle. For example, fuel tank 144 may store one or more liquid fuels, including but not limited to: gasoline, diesel, and alcohol fuels. In some examples, the fuel may be stored on-board the vehicle as a blend of two or more different fuels. For example, fuel tank 144 may be configured to store a blend of gasoline and ethanol (e.g., E10, E85, etc.) or a blend of gasoline and methanol (e.g., M10, M85, etc.), whereby these fuels or fuel blends may be delivered to engine 110 as indicated by arrow 142. Still other suitable fuels or fuel blends may be supplied to engine 110, where they may be combusted at the engine to produce an engine output. The engine output may be utilized to propel the vehicle as indicated by arrow 112 or to recharge energy storage device 150 via motor 120 or generator 160.

In some examples, energy storage device 150 may be configured to store electrical energy that may be supplied to other electrical loads residing on-board the vehicle (other than the motor), including cabin heating and air conditioning, engine starting, headlights, cabin audio and video systems, etc. As a non-limiting example, energy storage device 150 may include one or more batteries and/or capacitors.

Control system 190 may communicate with one or more of engine 110, motor 120, fuel system 140, energy storage device 150, and generator 160. Control system 190 may receive sensory feedback information from one or more of engine 110, motor 120, fuel system 140, energy storage device 150, and generator 160. Further, control system 190 may send control signals to one or more of engine 110, motor 120, fuel system 140, energy storage device 150, and generator 160 responsive to this sensory feedback. Control system 190 may receive an indication of an operator requested output of the vehicle propulsion system from a vehicle operator 102. For example, control system 190 may receive sensory feedback from pedal position sensor 194 which communicates with pedal 192. Pedal 192 may refer schematically to a brake pedal and/or an accelerator pedal. Furthermore, in some examples control system 190 may be in communication with a remote engine start receiver 195 (or transceiver) that receives wireless signals 106 from a key fob 104 having a remote start button 105. In other examples (not shown), a remote engine start may be initiated via a cellular telephone, or smartphone based system where a user's cellular telephone sends data to a server and the server communicates with the vehicle to start the engine.

Energy storage device 150 may periodically receive electrical energy from a power source 180 residing external to the vehicle (e.g., not part of the vehicle) as indicated by arrow 184. As a non-limiting example, vehicle propulsion system 100 may be configured as a plug-in hybrid electric vehicle (HEV), whereby electrical energy may be supplied to energy storage device 150 from power source 180 via an electrical energy transmission cable 182. During a recharging operation of energy storage device 150 from power source 180, electrical transmission cable 182 may electrically couple energy storage device 150 and power source 180. While the vehicle propulsion system is operated to propel the vehicle, electrical transmission cable 182 may disconnected between power source 180 and energy storage device 150. Control system 190 may identify and/or control the amount of electrical energy stored at the energy storage device, which may be referred to as the state of charge (SOC).

In other examples, electrical transmission cable 182 may be omitted, where electrical energy may be received wirelessly at energy storage device 150 from power source 180. For example, energy storage device 150 may receive electrical energy from power source 180 via one or more of electromagnetic induction, radio waves, and electromagnetic resonance. As such, it should be appreciated that any suitable approach may be used for recharging energy storage device 150 from a power source that does not comprise part of the vehicle. In this way, motor 120 may propel the vehicle by utilizing an energy source other than the fuel utilized by engine 110.

Fuel system 140 may periodically receive fuel from a fuel source residing external to the vehicle. As a non-limiting example, vehicle propulsion system 100 may be refueled by receiving fuel via a fuel dispensing device 170 as indicated by arrow 172. In some examples, fuel tank 144 may be configured to store the fuel received from fuel dispensing device 170 until it is supplied to engine 110 for combustion. In some examples, control system 190 may receive an indication of the level of fuel stored at fuel tank 144 via a fuel level sensor. The level of fuel stored at fuel tank 144 (e.g., as identified by the fuel level sensor) may be communicated to the vehicle operator, for example, via a fuel gauge or indication in a vehicle instrument panel 196.

The vehicle propulsion system 100 may also include an ambient temperature/humidity sensor 198, and a roll stability control sensor, such as a lateral and/or longitudinal and/or yaw rate sensor(s) 199. The vehicle instrument panel 196 may include indicator light(s) and/or a text-based display in which messages are displayed to an operator. The vehicle instrument panel 196 may also include various input portions for receiving an operator input, such as buttons, touch screens, voice input/recognition, etc. For example, the vehicle instrument panel 196 may include a refueling button 197 which may be manually actuated or pressed by a vehicle operator to initiate refueling. For example, as described in more detail below, in response to the vehicle operator actuating refueling button 197, a fuel tank in the vehicle may be depressurized so that refueling may be performed.

Control system 190 may be communicatively coupled to other vehicles or infrastructures using appropriate communications technology, as is known in the art. For example, control system 190 may be coupled to other vehicles or infrastructures via a wireless network 131, which may comprise Wi-Fi, Bluetooth, a type of cellular service, a wireless data transfer protocol, and so on. Control system 190 may broadcast (and receive) information regarding vehicle data, vehicle diagnostics, traffic conditions, vehicle location information, vehicle operating procedures, etc., via vehicle-to-vehicle (V2V), vehicle-to-infrastructure-to-vehicle (V2I2V), and/or vehicle-to-infrastructure (V2I) technology. The communication and the information exchanged between vehicles can be either direct between vehicles, or can be multi-hop. In some examples, longer range communications (e.g. WiMax) may be used in place of, or in conjunction with, V2V, or V2I2V, to extend the coverage area by a few miles. In still other examples, vehicle control system 190 may be communicatively coupled to other vehicles or infrastructures via a wireless network 131 and the internet (e.g. cloud), as is commonly known in the art.

Vehicle system 100 may also include an on-board navigation system 132 (for example, a Global Positioning System) that an operator of the vehicle may interact with. The navigation system 132 may include one or more location sensors for assisting in estimating vehicle speed, vehicle altitude, vehicle position/location, etc. This information may be used to infer engine operating parameters, such as local barometric pressure. As discussed above, control system 190 may further be configured to receive information via the internet or other communication networks. Information received from the GPS may be cross-referenced to information available via the internet to determine local weather conditions, local vehicle regulations, etc. In one example, information received from the GPS may be utilized in conjunction with route learning methodology, such that routes commonly traveled by a vehicle may be learned by the vehicle control system 190. In some examples, other sensors, such as lasers, radar, sonar, acoustic sensors, etc., (e.g. 133) may be additionally or alternatively utilized in conjunction with the onboard navigation system to conduct route learning of commonly traveled routes by the vehicle.

Vehicle system 100 may also include sensors dedicated to indicating the occupancy-state of the vehicle, for example seat load cells 107, door sensing technology 108, and onboard cameras 109.

FIG. 2 shows a schematic depiction of a vehicle system 206. It may be understood that vehicle system 206 may comprise the same vehicle system as vehicle system 100 depicted at FIG. 1. The vehicle system 206 includes an engine system 208 coupled to an emissions control system 251 and a fuel system 218. It may be understood that fuel system 218 may comprise the same fuel system as fuel system 140 depicted at FIG. 1. Emission control system 251 includes a fuel vapor container or canister 222 which may be used to capture and store fuel vapors. In some examples, vehicle system 206 may be a hybrid electric vehicle system.

The engine system 208 may include an engine 110 having a plurality of cylinders 230. While not explicitly shown, it may be understood that each cylinder may include one or more intake valve(s) and one or more exhaust valve(s). The engine 110 includes an engine air intake 223 and an engine exhaust 225. The engine air intake 223 includes a throttle 262 in fluidic communication with engine intake manifold 244 via an intake passage 242. The throttle 262 may comprise an electronic throttle, which may be controlled via the vehicle controller sending a signal to actuate the throttle to a desired position. In such an example where the throttle is electronic, power to control the throttle to the desired position may be from an onboard energy storage device (e.g. 150), such as a battery. Further, engine air intake 223 may include an air box and filter 215 positioned upstream of throttle 262. The engine exhaust system 225 includes an exhaust manifold 248 leading to an exhaust passage 235 that routes exhaust gas to the atmosphere. The engine exhaust system 225 may include one or more emission control devices, or exhaust catalyst 270, which may be mounted in a close-coupled position in the exhaust. The one or more emission control devices may include a three-way catalyst, lean NOx trap, diesel particulate filter, oxidation catalyst, etc. It will be appreciated that other components may be included in the engine such as a variety of valves and sensors. For example, a barometric pressure sensor 213 may be included in the engine intake. In one example, barometric pressure sensor 213 may be a manifold air pressure (MAP) sensor and may be coupled to the engine intake downstream of throttle 262. Barometric pressure sensor 213 may rely on part throttle or full or wide open throttle conditions, e.g., when an opening amount of throttle 262 is greater than a threshold, in order accurately determine BP. Alternatively, MAP may be inferred from alternate engine operating conditions, such as mass air flow (MAF), as measured by MAF sensor 210 coupled to the intake manifold.

Engine exhaust system 225 may further include a gasoline particulate filter (GPF) 217. GPF 217 may comprise a particulate filter, hydrocarbon trap, a catalyzed wash coat, or combination thereof. In some examples, during operation of engine 110, GPF 217 may be periodically regenerated by operating at least one cylinder of the engine within a particular air-fuel ratio to increase a temperature of GPF 217, such that retained hydrocarbons and soot particles may be oxidized.

In some examples, temperature sensor 226 may be positioned upstream from the inlet of GPF 217 and temperature sensor 229 may be positioned downstream of GPF 217. Temperature sensors 226 and 229 may be used to assess the temperature of GPF 217 for regeneration purposes, for example. Furthermore, pressure in the exhaust system may be assessed by pressure sensor 263. Pressure sensor 263 may be a differential pressure sensor positioned upstream and downstream of GPF 217, for example. Pressure sensor 263 may be used to determine pressure at the inlet of GPF 217 in order to assess operating conditions for air to be introduced to the inlet of GPF 217 for regeneration. Furthermore, in some examples, soot sensor 268 may be positioned downstream of GPF 217, to assess the level of soot that is released from GPF 217. Soot sensor 268 may be used to diagnose operation of GPF 217, among other functions.

Fuel system 218 may include a fuel tank 220 coupled to a fuel pump system 221. It may be understood that fuel tank 220 may comprise the same fuel tank as fuel tank 144 depicted above at FIG. 1. The fuel pump system 221 may include one or more pumps for pressurizing fuel delivered to the injectors of engine 110, such as the example injector 266 shown. While only a single injector 266 is shown, additional injectors are provided for each cylinder. It will be appreciated that fuel system 218 may be a return-less fuel system, a return fuel system, or various other types of fuel system. Fuel tank 220 may hold a plurality of fuel blends, including fuel with a range of alcohol concentrations, such as various gasoline-ethanol blends, including E10, E85, gasoline, etc., and combinations thereof. A fuel level sensor 234 located in fuel tank 220 may provide an indication of the fuel level ("Fuel Level Input") to controller 212. As depicted, fuel level sensor 234 may comprise a float connected to a variable resistor. Alternatively, other types of fuel level sensors may be used.

Vapors generated in fuel system 218 may be routed to an evaporative emissions control system 251 which includes a fuel vapor canister 222 via vapor recovery line 231, before being purged to the engine air intake 223. Vapor recovery line 231 may be coupled to fuel tank 220 via one or more conduits and may include one or more valves for isolating the fuel tank during certain conditions. For example, vapor recovery line 231 may be coupled to fuel tank 220 via one or more or a combination of conduits 271, 273, and 275.

Further, in some examples, one or more fuel tank vent valves may be positioned in conduits 271, 273, or 275. Among other functions, fuel tank vent valves may allow a fuel vapor canister of the emissions control system to be maintained at a low pressure or vacuum without increasing the fuel evaporation rate from the tank (which would otherwise occur if the fuel tank pressure were lowered). For example, conduit 271 may include a grade vent valve (GVV) 287, conduit 273 may include a fill limit venting valve (FLVV) 285, and conduit 275 may include a grade vent valve (GVV) 283. Further, in some examples, recovery line 231 may be coupled to a fuel filler system 219. In some examples, fuel filler system may include a fuel cap 205 for sealing off the fuel filler system from the atmosphere. Refueling system 219 is coupled to fuel tank 220 via a fuel filler pipe or neck 211.

Further, refueling system 219 may include refueling lock 245. In some examples, refueling lock 245 may be a fuel cap locking mechanism. The fuel cap locking mechanism may be configured to automatically lock the fuel cap in a closed position so that the fuel cap cannot be opened. For example, the fuel cap 205 may remain locked via refueling lock 245 while pressure or vacuum in the fuel tank is greater than a threshold. In response to a refuel request, e.g., a vehicle operator initiated request, the fuel tank may be depressurized and the fuel cap unlocked after the pressure or vacuum in the fuel tank falls below a threshold. A fuel cap locking mechanism may be a latch or clutch, which, when engaged, prevents the removal of the fuel cap. The latch or clutch may be electrically locked, for example, by a solenoid, or may be mechanically locked, for example, by a pressure diaphragm.

In some examples, refueling lock 245 may be a filler pipe valve located at a mouth of fuel filler pipe 211. In such examples, refueling lock 245 may not prevent the removal of fuel cap 205. Rather, refueling lock 245 may prevent the insertion of a refueling pump into fuel filler pipe 211. The filler pipe valve may be electrically locked, for example by a solenoid, or mechanically locked, for example by a pressure diaphragm.

In some examples, refueling lock 245 may be a refueling door lock, such as a latch or a clutch which locks a refueling door located in a body panel of the vehicle. The refueling door lock may be electrically locked, for example by a solenoid, or mechanically locked, for example by a pressure diaphragm.

In examples where refueling lock 245 is locked using an electrical mechanism, refueling lock 245 may be unlocked by commands from controller 212, for example, when a fuel tank pressure decreases below a pressure threshold. In examples where refueling lock 245 is locked using a mechanical mechanism, refueling lock 245 may be unlocked via a pressure gradient, for example, when a fuel tank pressure decreases to atmospheric pressure.

Emissions control system 251 may include one or more emissions control devices, such as one or more fuel vapor canisters 222 filled with an appropriate adsorbent 286b, the canisters are configured to temporarily trap fuel vapors (including vaporized hydrocarbons) during fuel tank refilling operations and "running loss" (that is, fuel vaporized during vehicle operation). In one example, the adsorbent 286b used is activated charcoal. Emissions control system 251 may further include a canister ventilation path or vent line 227 which may route gases out of the canister 222 to the atmosphere when storing, or trapping, fuel vapors from fuel system 218.

Canister 222 may include a buffer 222a (or buffer region), each of the canister and the buffer comprising the adsorbent. As shown, the volume of buffer 222a may be smaller than (e.g., a fraction of) the volume of canister 222. The adsorbent 286a in the buffer 222a may be same as, or different from, the adsorbent in the canister (e.g., both may include charcoal). Buffer 222a may be positioned within canister 222 such that during canister loading, fuel tank vapors are first adsorbed within the buffer, and then when the buffer is saturated, further fuel tank vapors are adsorbed in the canister. In comparison, during canister purging, fuel vapors are first desorbed from the canister (e.g., to a threshold amount) before being desorbed from the buffer. In other words, loading and unloading of the buffer is not linear with the loading and unloading of the canister. As such, the effect of the canister buffer is to dampen any fuel vapor spikes flowing from the fuel tank to the canister, thereby reducing the possibility of any fuel vapor spikes going to the engine. One or more temperature sensors 232 may be coupled to and/or within canister 222. As fuel vapor is adsorbed by the adsorbent in the canister, heat is generated (heat of adsorption). Likewise, as fuel vapor is desorbed by the adsorbent in the canister, heat is consumed. In this way, the adsorption and desorption of fuel vapor by the canister may be monitored and estimated based on temperature changes within the canister.

Vent line 227 may also allow fresh air to be drawn into canister 222 when purging stored fuel vapors from fuel system 218 to engine intake 223 via purge line 228 and purge valve 261. For example, purge valve 261 may be normally closed but may be opened during certain conditions so that vacuum from engine intake manifold 244 is provided to the fuel vapor canister for purging. In some examples, vent line 227 may include an air filter 259 disposed therein upstream of a canister 222.

In some examples, the flow of air and vapors between canister 222 and the atmosphere may be regulated by a canister vent valve 297 coupled within vent line 227. When included, the canister vent valve 297 may be a normally open valve, so that fuel tank isolation valve 252 (FTIV) may control venting of fuel tank 220 with the atmosphere. FTIV 252 may be positioned between the fuel tank and the fuel vapor canister 222 within conduit 278. FTIV 252 may be a normally closed valve, that when opened, allows for the venting of fuel vapors from fuel tank 220 to fuel vapor canister 222. Fuel vapors may then be vented to atmosphere, or purged to engine intake system 223 via canister purge valve 261. As will be discussed in detail below, in some example the FTIV may not be included, whereas in other examples, an FTIV may be included.

Fuel system 218 may be operated by controller 212 in a plurality of modes by selective adjustment of the various valves and solenoids. It may be understood that control system 214 may comprise the same control system as control system 190 depicted above at FIG. 1. For example, the fuel system may be operated in a fuel vapor storage mode (e.g., during a fuel tank refueling operation and with the engine not combusting air and fuel), wherein the controller 212 may open isolation valve 252 (when included) while closing canister purge valve (CPV) 261 to direct refueling vapors into canister 222 while preventing fuel vapors from being directed into the intake manifold.

As another example, the fuel system may be operated in a refueling mode (e.g., when fuel tank refueling is requested by a vehicle operator), wherein the controller 212 may open isolation valve 252 (when included), while maintaining canister purge valve 261 closed, to depressurize the fuel tank before allowing enabling fuel to be added therein. As such, isolation valve 252 (when included) may be kept open during the refueling operation to allow refueling vapors to be stored in the canister. After refueling is completed, the isolation valve may be closed.

As yet another example, the fuel system may be operated in a canister purging mode (e.g., after an emission control device light-off temperature has been attained and with the engine combusting air and fuel), wherein the controller 212 may open canister purge valve 261 while closing isolation valve 252 (when included). Herein, the vacuum generated by the intake manifold of the operating engine may be used to draw fresh air through vent 227 and through fuel vapor canister 222 to purge the stored fuel vapors into intake manifold 244. In this mode, the purged fuel vapors from the canister are combusted in the engine. The purging may be continued until the stored fuel vapor amount in the canister is below a threshold.

Controller 212 may comprise a portion of a control system 214. In some examples, control system 214 may be the same as control system 190, illustrated in FIG. 1. Control system 214 is shown receiving information from a plurality of sensors 216 (various examples of which are described herein) and sending control signals to a plurality of actuators 281 (various examples of which are described herein). As one example, sensors 216 may include exhaust gas sensor 237 located upstream of the emission control device 270, temperature sensor 233, pressure sensor 291, pressure sensor 282, canister temperature sensor 232, MAF sensor 210, and pressure sensor 263. Other sensors such as pressure, temperature, air/fuel ratio, and composition sensors may be coupled to various locations in the vehicle system 206. As another example, the actuators may include throttle 262, fuel tank isolation valve 252, canister purge valve 261, and canister vent valve 297. The controller may receive input data from the various sensors, process the input data, and trigger the actuators in response to the processed input data based on instruction or code programmed therein corresponding to one or more routines. Example control routines are described herein with regard to FIGS. 6-7.

In some examples, the controller may be placed in a reduced power mode or sleep mode, wherein the controller maintains essential functions only, and operates with a lower battery consumption than in a corresponding awake mode. For example, the controller may be placed in a sleep mode following a vehicle-off event in order to perform a diagnostic routine at a duration after the vehicle-off event. The controller may have a wake input that allows the controller to be returned to an awake mode based on an input received from one or more sensors. For example, the opening of a vehicle door may trigger a return to an awake mode, or a remote start event may trigger a return to an awake mode. In other examples, particularly with regard to the methods depicted in FIGS. 6-7, the controller may be required to be awake in order to conduct such methods. For example, a wakeup capability may enable a circuit to wake the controller in order to obtain baseline comparator data, or to conduct an engine system diagnostic, as will be discussed in further detail below.

Undesired evaporative emissions detection routines may be intermittently performed by controller 212 on fuel system 218 and/or evaporative emissions system 251 to confirm that undesired evaporative emissions are not present in the fuel system and/or evaporative emissions system. As such, evaporative emissions detection routines may be performed while the engine is off (engine-off test) using engine-off natural vacuum (EONV) generated due to a change in temperature and pressure at the fuel tank following engine shutdown and/or with vacuum supplemented from a vacuum pump. Alternatively, evaporative emissions detection routines may be performed while the engine is running by operating a vacuum pump and/or using engine intake manifold vacuum. In some configurations, a canister vent valve (CVV) 297 may be coupled within vent line 227. CVV 297 may function to adjust a flow of air and vapors between canister 222 and the atmosphere. The CVV may also be used for diagnostic routines. When included, the CVV may be opened during fuel vapor storing operations (for example, during fuel tank refueling and while the engine is not running) so that air, stripped of fuel vapor after having passed through the canister, can be pushed out to the atmosphere. Likewise, during purging operations (for example, during canister regeneration and while the engine is running), the CVV may be opened to allow a flow of fresh air to strip the fuel vapors stored in the canister. In some examples, CVV 297 may be a solenoid valve wherein opening or closing of the valve is performed via actuation of a canister vent solenoid. In particular, the canister vent valve may be an open that is closed upon actuation of the canister vent solenoid. In some examples, CVV 297 may be configured as a latchable solenoid valve. In other words, when the valve is placed in a closed configuration, it latches closed without requiring additional current or voltage. For example, the valve may be closed with a 100 ms pulse, and then opened at a later time point with another 100 ms pulse. In this way, the amount of battery power required to maintain the CVV closed is reduced.

In another example, an engine system diagnostic may be conducted in order to determine whether a source of degradation stems from an intake manifold of the engine, an exhaust system of the engine, or the engine itself. Such an example will be discussed in detail below with regard to the methods depicted at FIGS. 6-7. Discussed herein, degradation of the intake manifold may refer to a puncture, crack, degraded gasket, loose coupling, or air leak in the intake manifold. Degradation of the exhaust system may similarly refer to a puncture, crack, degraded gasket, loose coupling, or exhaust leak in the exhaust system. It may be understood that degradation of the exhaust system may refer to the engine system upstream of the GPF (e.g. 217) or differential pressure sensor (e.g. 263), and downstream of the engine (e.g. 110). Finally, degradation of the engine may refer to intake/exhaust valves that are not sealing properly, undesired camshaft timing, compression issues, or any other engine-specific issues which may result in the engine not pumping as effectively as expected or demanded.

Turning now to FIGS. 3A-3C, they illustrate examples of sources of degradation stemming from the intake manifold, exhaust system, or engine, respectively. Accordingly, FIGS. 3A-3C illustrate simplified block diagrams of the engine system comprising MAF sensor 210, intake manifold 244, engine 110, exhaust system 225, GPF 217, and differential pressure sensor 263. As such, FIGS. 3A-3C represent simplified block diagrams of the engine system depicted above at FIG. 2. In each of FIGS. 3A-3C, as will be elaborated below, a source of degradation is illustrated, denoted as 310a, 310b, and 310c.

Turning now to FIG. 3A, it shows an example where a source of degradation 310a is stemming from intake manifold 244. In such an example, the source of degradation 310a is not directly observable via MAF sensor 210, as the source of degradation is downstream of MAF sensor 210. However, while the engine is in operation, unmetered air may be drawn into the engine via the source of degradation. Thus, it may be understood that additional air (in addition to that drawn through the intake passage (e.g. 242) may be drawn into the engine, and accordingly pressure in the exhaust system may be greater than expected, as monitored by the differential pressure sensor 263. Accordingly, as will be discussed in further detail below with regard to FIGS. 6-9, it may be possible in such an example to diagnose the source of degradation 310a in the intake manifold 244 if air flow as indicated via MAF sensor 210 is substantially equivalent to an expected air flow under a set of predetermined conditions, but where exhaust flow (e.g. pressure in the exhaust system) as indicated by differential pressure sensor 263, is greater than an expected exhaust flow under the same (or substantially equivalent) set of predetermined conditions. Such an example may involve spinning the engine unfueled in a forward direction to obtain the MAF sensor data and the differential pressure sensor data. In other words, the exhaust flow as indicated by differential pressure sensor 263 may be greater than expected due to the unmetered air being drawn into the engine and through the exhaust system via the source of degradation 310a when the engine is spun unfueled in the forward direction.

In another example, it may additionally or alternatively be possible to diagnose a source of degradation in the intake manifold by first spinning the engine unfueled in the forward or default direction and monitoring air flow in the intake system via the MAF sensor, and then spinning the engine unfueled in the reverse direction and again monitoring air flow in the intake system via the MAF sensor. In such an example, if there is a source of degradation 310a in the intake manifold, then MAF sensor data recorded while spinning the engine unfueled in the forward direction may be greater than the MAF sensor data recorded while spinning the engine unfueled in reverse, as less air flow may reach the MAF sensor due to the source of degradation 310a, when the engine is spun unfueled in reverse. In other words, when spinning the engine unfueled in the forward direction, the MAF sensor 210 may not detect unmetered air which may be drawn into the engine via the source of degradation 310a. However, when the engine is spun in reverse, the air flow generated in the intake by spinning the engine in reverse may at least partially exit through the source of degradation 310a, thus resulting in less air flow as monitored via the MAF sensor, than expected (for example compared to baseline measurements in the absence of degradation).

Turning now to FIG. 3B, it shows an example where a source of degradation 310b is stemming from the exhaust system 225. In such an example, the source of degradation is not directly observable via MAF sensor 210, or differential pressure sensor 263, alone. However, while the engine is in operation, for example being spun unfueled in the forward direction, exhaust flow may be pushed or forced to atmosphere via the source of degradation 310b, resulting in an overall less exhaust flow as monitored via the differential pressure sensor 263. Accordingly, as will be discussed in further detail below with regard to FIGS. 6-9, it may be possible to diagnose a source of degradation in the exhaust system 225 if mass air flow as indicated via MAF sensor 210 is substantially equivalent to an expected mass air flow under a set of predetermined conditions, but where exhaust flow (e.g. pressure in the exhaust system) as indicated by differential pressure sensor 263, is less than an expected exhaust flow under the same (or substantially equivalent) set of predetermined conditions.

Turning now to FIG. 3C, it shows an example where a source of degradation 310c is stemming from engine 110. As mentioned above, a source of degradation 310c stemming from the engine 110 may comprise intake/exhaust valves that are not sealing properly, undesired camshaft timing, compression issues, or any other engine-specific issues which may result in the engine not pumping as effectively as expected or demanded. In such an example, MAF sensor 210 may not directly be used to infer a source of degradation stemming from the engine, and similarly differential pressure sensor 263 may not directly be used to infer such a source of degradation. However, an engine with a source of degradation may not pump as efficiently as expected, and as such, an amount of air drawn into the intake passage (e.g. 242) may be lower than expected under a set of predetermined conditions. Similarly, because less air overall was drawn into the engine via the intake passage, then less exhaust flow may occur as a result. Accordingly, as will be discussed in further detail below with regard to FIGS. 6-9, it may be possible to diagnose a source of degradation stemming from engine 110 if intake mass air flow as indicated by MAF sensor 210 is substantially equivalent to exhaust flow as indicated by differential pressure sensor 263, but where both intake mass air flow and exhaust flow are lower than expected under a set of predetermined conditions where the engine is spun unfueled in the forward direction.

In another example, it may be possible to diagnose the source of degradation stemming from engine 110 if air flow in the intake as monitored via the MAF sensor when the engine is spun unfueled in the forward direction is substantially equivalent to air flow in the intake as monitored via the MAF sensor when the engine is spun unfueled in the reverse direction, but where the air flow in response to the engine being spun in both the forward and reverse directions is lower than expected (e.g. lower than baseline comparator data).

The set of predetermined conditions, as discussed above with regard to FIGS. 3A-3C may include engine speed at a predetermined speed (e.g. predetermined RPM), a position of a throttle (e.g. 262) at a predetermined angle or level of opening, the engine being rotated or spun unfueled via power from an onboard energy storage device (e.g. 150), etc. Furthermore, as discussed above, "expected" amounts of air flow in the intake manifold and exhaust system may comprise air flow amounts that have been previously established during conditions where no source of degradation is indicated, under conditions of spinning the engine unfueled in both the forward and reverse directions. In other words, as will be discussed in further detail below, expected amounts of air flow in the intake (under forward and reverse engine spinning) and exhaust system (under forward engine spinning) may comprise baseline air flow in the intake manifold and baseline air flow in the exhaust system, under a substantially equivalent set of predetermined conditions as that discussed above with regard to FIGS. 3A-3C.

As discussed, systems and methods for diagnosing the engine system may include rotating or spinning the engine unfueled to establish baseline, or expected, air flow in the intake manifold and exhaust system under conditions where degradation is not already indicated. Furthermore, when conducting the engine system diagnostic comprising comparing values obtained via the MAF sensor 210 and differential pressure sensor 263, the systems and methods may similarly include rotating or spinning the engine unfueled. Accordingly, to avoid customer dissatisfaction due to the engine being spun without being fueled, such an engine system diagnostic may execute under conditions where a vehicle operator and passengers are not indicated to be in the vehicle. Examples may include a remote start event when the vehicle is not occupied, a "wake-up" of the vehicle controller some predetermined duration after a key-off event where the vehicle is not occupied, immediately after a key-off where the controller is maintained awake to conduct the diagnostic, etc. In still another example, the engine system diagnostic may be conducted in an autonomous vehicle in which the vehicle is indicated to be unoccupied. In each of the above-mentioned examples, vehicle occupancy may be indicated by one or more of seat load cells (e.g. 107, door sensing technology (e.g. 108), and/or onboard camera(s) (e.g. 109).

As the engine system diagnostic discussed above may be conducted in a vehicle configured as an autonomous vehicle, an example autonomous driving system is discussed below with regard to FIG. 4. FIG. 4 is a block diagram of an example autonomous driving system 400 that may operate the vehicle system 100, described above at FIG. 1. Herein, the vehicle system 100 will be referred to simply as a "vehicle". The autonomous driving system 400, as shown, includes a user interface device 410, a navigation system 415, at least one autonomous driving sensor 420, and an autonomous mode controller 425. It may be understood that the onboard navigation system 415 may be the same as the onboard navigation system 132 depicted above at FIG. 1.

The user interface device 410 may be configured to present information to vehicle occupants, under conditions wherein a vehicle occupant may be present. However, it may be understood that the vehicle may be operated autonomously in the absence of vehicle occupants, under certain conditions. The presented information may include audible information or visual information. Moreover, the user interface device 410 may be configured to receive user inputs. Thus, the user interface device 410 may be located in the passenger compartment (not shown) of the vehicle. In some possible approaches, the user interface device 410 may include a touch-sensitive display screen.

The navigation system 415 may be configured to determine a current location of the vehicle using, for example, a Global Positioning System (GPS) receiver configured to triangulate the position of the vehicle relative to satellites or terrestrial based transmitter towers. The navigation system 415 may be further configured to develop routes from the current location to a selected destination, as well as display a map and present driving directions to the selected destination via, for example, the user interface device 410.

The autonomous driving sensors 420 may include any number of devices configured to generate signals that help navigate the vehicle. Examples of autonomous driving sensors 420 may include a radar sensor, a lidar sensor, a vision sensor (e.g. a camera), vehicle to vehicle infrastructure networks, or the like. The autonomous driving sensors 420 may enable the vehicle to "see" the roadway and vehicle surroundings, and/or negotiate various obstacles while the vehicle 100 is operating in autonomous mode. The autonomous driving sensors 420 may be configured to output sensor signals to, for example, the autonomous mode controller 425.

The autonomous mode controller 425 may be configured to control one or more subsystems 430 while the vehicle is operating in the autonomous mode. Examples of subsystems 430 that may be controlled by the autonomous mode controller 425 may include a brake subsystem, a suspension subsystem, a steering subsystem, and a powertrain subsystem. The autonomous mode controller 425 may control any one or more of these subsystems 430 by outputting signals to control units associated with subsystems 430. In one example, the brake subsystem may comprise an anti-lock braking subsystem, configured to apply a braking force to one or more of wheels (e.g. 135). Discussed herein, applying the braking force to one or more of the vehicle wheels may be referred to as activating the brakes. To autonomously control the vehicle, the autonomous mode controller 425 may output appropriate commands to the subsystems 430. The commands may cause the subsystems to operate in accordance with the driving characteristics associated with the selected driving mode. For example, driving characteristics may include how aggressively the vehicle accelerates and decelerates, how much space the vehicle leaves behind a front vehicle, how frequently the autonomous vehicle changes lanes, etc.

Figure 5A:
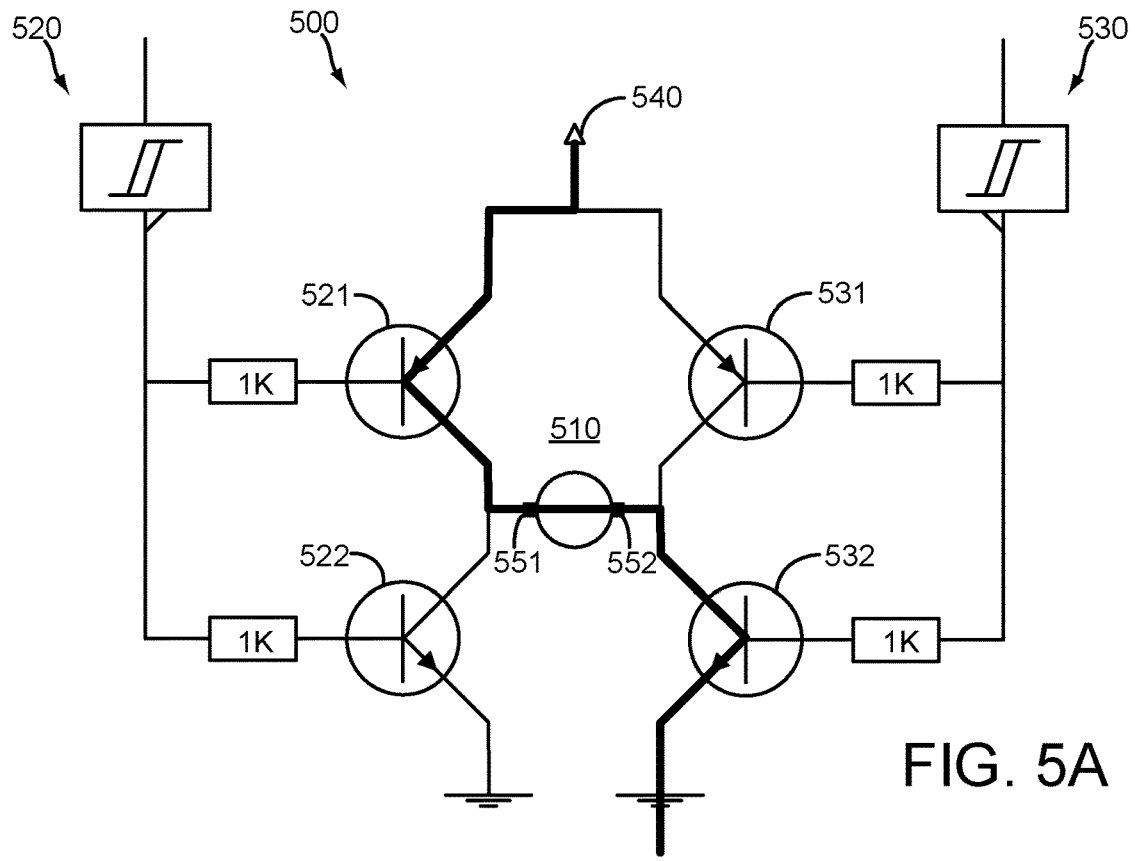
FIGS. 5A-5B schematically shows an example H-bridge circuit which may be used to rotate a vehicle engine in a forward or reverse direction.
Figure 5B:
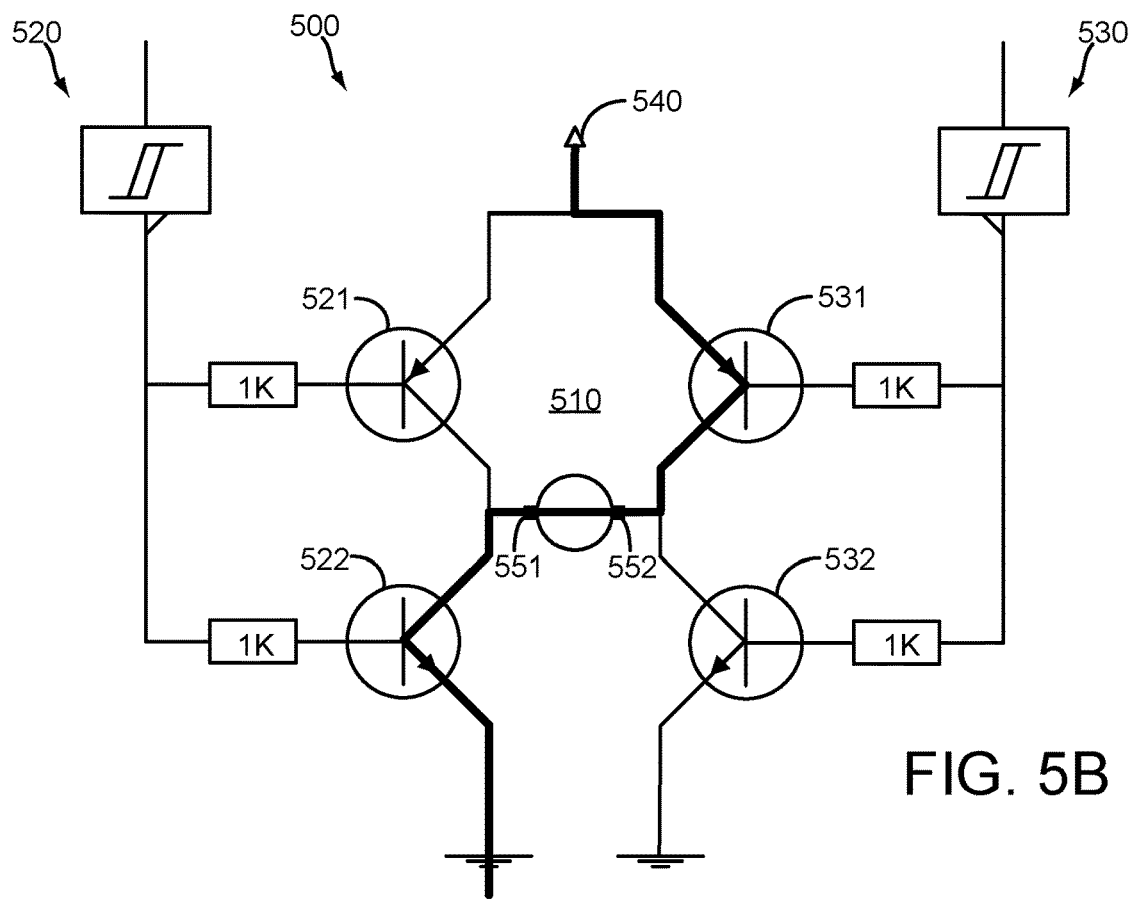

FIGS. 5A and 5B show an example circuit 500 that may be used for reversing a spin orientation of an electric motor. Circuit 500 schematically depicts an H-Bridge circuit that may be used to run a motor 510 in a first (forward) direction and alternately in a second (reverse) direction. Circuit 500 comprises a first (LO) side 520 and a second (HI) side 530. Side 520 includes transistors 521 and 522, while side 530 includes transistors 531 and 532. Circuit 500 further includes a power source 540.

In FIG. 5A, transistors 521 and 532 are activated (energized), while transistors 522 and 531 are off. In this configuration, the left lead 551 of motor 510 is connected to power source 540, and the right lead 552 of motor 510 is connected to ground. In this way, motor 500 may run in a forward (or default) direction. When operating the engine in a forward direction via the motor, the engine may be in a cranking mode for initial combustion commencement. Additionally and/or alternatively, when operating the engine in a forward direction via the motor, the engine (and motor or another motor) may be in a drive mode to drive the vehicle. It may be understood that in some examples, the engine may be spun in the forward (e.g. default) direction under conditions where the vehicle is stationary and it is desired only for the engine to be spun or rotated in the forward direction, without combustion.

In FIG. 5B, transistors 522 and 531 are activated (energized), while transistors 521 and 532 are off. In this configuration, the right lead 552 of motor 510 is connected to power source 540, and the left lead 551 of motor 510 is connected to ground. In this way, motor 510 may run in a reverse direction.

Turning now to FIG. 6, a high level example method 600 for conducting an engine system diagnostic, is shown. More specifically, method 600 may be used to diagnose the presence or absence of degradation stemming from an intake manifold, exhaust system, or engine of a vehicle, by comparing air flow in the intake system and air flow in the exhaust system under a set of predetermined conditions to a baseline air flow in the intake system and a baseline air flow in the exhaust system (under a substantially equivalent set of predetermined conditions). In this way, sources of degradation may be pinpointed as to being either in the intake manifold, exhaust system, or engine compartment. By pinpointing a source of degradation, repair procedures may be streamlined, and operational issues related to the engine system may be diagnosed rapidly and precisely, which may result in an increased lifespan of engine system componentry.

Method 600 will be described with reference to the systems described herein and shown in FIGS. 1-5B, though it should be understood that similar methods may be applied to other systems without departing from the scope of this disclosure. Method 600 may be carried out by a controller, such as controller 212 in FIG. 2, and may be stored at the controller as executable instructions in non-transitory memory. Instructions for carrying out method 600 and the rest of the methods included herein may be executed by the controller based on instructions stored on a memory of the controller and in conjunction with signals received from sensors of the engine system, such as the sensors described above with reference to FIGS. 1-4. The controller may employ engine system actuators, such as motor (e.g. 120), throttle (e.g. 262), canister purge valve (e.g. 261), etc., according to the method below.

Method 600 begins at 605 and may include indicating whether conditions are met for obtaining baseline comparator data for the engine system diagnostic, where baseline comparator data includes measurements of air flow in the intake system under conditions of forward and reverse engine spinning, as well as measurements of air flow in the exhaust system under conditions of forward, and in some examples, reverse engine spinning. Conditions being met for obtaining baseline comparator data may include an indication that the vehicle is not occupied. As discussed above, seat load cells, onboard camera(s), and/or door sensing technology may be utilized to ensure that the vehicle is not occupied. Baseline comparator data may be thus obtained responsive to a remote start event, or a wakeup of the controller a predetermined duration after a key-off event, or in a case where the vehicle comprises an autonomous vehicle that is unoccupied and not in motion. More specifically, if the vehicle is in operation, for example if the vehicle is being propelled via either a motor (e.g. 120), engine (e.g. 110), or some combination thereof, conditions may not be indicated to be met for obtaining baseline comparator data for the engine system diagnostic. Still further, conditions being indicated to be met at 605 may include an indication that a source of degradation is not already indicated to be present in the intake manifold, exhaust system, or engine of the vehicle. For example, baseline comparator data may be obtained initially on a new engine system, where it is established that no part of the engine system is degraded. Subsequently, in the absence of an indication otherwise (e.g. sudden lean air/fuel ratio), baseline data may be periodically acquired via the controller on the non-degraded engine system. In the case of a sudden air/fuel ratio shift, then the baseline comparator data to be utilized for conducting the engine system test diagnostic (discussed below) may comprise the most recent baseline comparator data prior to the air/fuel ratio shift.

Furthermore, conditions being met at 605 for obtaining baseline comparator data may include an indication that baseline comparator data has not been obtained for a predetermined duration of time since a prior baseline comparator data measurement. In some examples, such a predetermined duration of time may comprise 1 day, greater than 1 day but less than 2 days, greater than 2 days but less than 5 days, greater than 5 days but less than 10 days, greater than 10 days, etc. If, at 605, it is indicated that conditions are indicated to be met for obtaining baseline comparator data, method 600 may proceed to 610, where baseline comparator data may be obtained according to method 700 depicted at FIG. 7.

Alternatively, if conditions are not indicated to be met at 605 for obtaining baseline comparator data, method 600 may proceed to 615, and may include indicating whether conditions are met for conducting the engine system diagnostic. Conditions being met for conducting the engine system diagnostic may similarly include an indication that the vehicle is not occupied, which may include a remote start event, a controller wake-up a predetermined duration after a key-off event, or an unoccupied autonomous vehicle. Furthermore, conditions being met for conducting the engine system diagnostic at 615 may include an indication that baseline comparator data has been obtained within a threshold duration of the engine system diagnostic that is desired to be conducted at 615. In some examples, the threshold duration since baseline comparator data has been obtained may comprise 1 day or less, greater than 1 day but less than 2 days, greater than 2 days but less than three days, etc. Still further, conditions being met for conducting the engine system diagnostic at 615 may include an indication that the air intake system filter (e.g. 215) has not been replaced since baseline comparator data has been obtained, and may further include an indication that the GPF (e.g. 217), where included, has not been regenerated since the baseline comparator data was obtained. Another example of conditions being met for conducting the engine system diagnostic includes an indication that a source of degradation is not already indicated to be present in the intake manifold, exhaust system, or engine of the vehicle.

In still further examples, conditions being met for conducting the engine system diagnostic may include an indication of a disturbance to an air-fuel ratio, as monitored via an exhaust gas sensor (e.g. 237). For example, if during a drive cycle where the engine is operating (e.g. combusting air and fuel), it is indicated that the engine system is running lean (or rich), one possibility may be that there is a source of degradation stemming from either the intake manifold, exhaust system, or engine. An indication the engine is operating too lean may be provided, for example, from a long term correction in combustion air/fuel ratio for a lean air/fuel bias. Accordingly, if the engine system indicates an unexpected air-fuel ratio, then such an indication may be stored at the controller. Such an indication being stored at the controller may trigger the engine system diagnostic to be conducted, provided that all conditions are met for conducting the engine system diagnostic at step 615 of method 600.

If, at step 615, it is indicated that conditions are not met for conducting the engine system diagnostic, method 600 may proceed to 620, and may include maintaining current vehicle operating parameters. For example, if the vehicle is not in operation, where the engine is off (not combusting air and fuel), and where the motor is not being utilized to propel the vehicle, then such conditions may be maintained. Alternatively, if the vehicle is in operation, then current vehicle operating parameters may be maintained. In an example case where an air-fuel ratio disturbance was indicated, and thus an engine system diagnostic is desired, but where conditions are not indicated to be met at 615, such an indication may be stored at the controller such that the engine system diagnostic may be triggered to be conducted responsive to conditions being met for conducting the engine system diagnostic. In a further example where one of the conditions not being indicated to be met at 615 includes the absence of appropriate baseline comparator data (e.g. baseline comparator data obtained greater than the threshold duration prior to execution of the engine system diagnostic, or conditions where the intake air filter (e.g. 215) was replaced or the GPF, where included, was regenerated subsequent to obtaining baseline comparator data), the method may include setting flag at the controller and illuminating a malfunction indicator light on a vehicle dash. Such an indication may alert the vehicle operator of a need to service the vehicle, for a potential source of degradation stemming from the intake manifold, exhaust system, or engine compartment, for example, because in the absence of appropriate baseline comparator data, the engine system diagnostic may not be conducted.

To prevent such a situation, in some examples, the vehicle controller may prevent GPF regeneration until an engine system diagnostic has been conducted, responsive to obtaining baseline comparator data. However, the controller may rely on pressure measurements as indicated via the differential pressure sensor (e.g. 263) to determine whether it is desirable to regenerate the GPF at the expense of an engine system diagnostic, or whether the GPF regeneration may be prevented until the engine system diagnostic has been conducted. For example, if, during engine operation, a threshold pressure differential (e.g. within 5-10% or less of a pressure differential indicating saturation of the GPF) is obtained via the differential pressure sensor (e.g. 263) corresponding to the GPF, then it may be determined that the GPF may be regenerated, even though such an event may result in the engine system diagnostic not being able to be conducted until subsequent baseline comparator data is obtained.

In a case where the GPF is regenerated subsequent to obtaining baseline comparator data, such that new baseline comparator data may be obtained, a flag may be set at the controller indicating that the GPF was regenerated subsequent to baseline comparator data being obtained, such that new baseline comparator data may be obtained at the next available opportunity (e.g. when conditions are met for obtaining baseline comparator data, as discussed above).

A similar situation may arise if the intake air filter (e.g. 215) is replaced subsequent to baseline comparator data being obtained. For example, a flag may be set at the controller under such circumstances, instructing the vehicle controller to subsequently obtain baseline comparator data at the next opportunity where conditions are indicated to be met for obtaining baseline comparator data.

Returning to step 615 of method 600, if conditions are indicated to be met for conducting the engine system diagnostic, method 600 may proceed to 625, and may include conducting the engine system diagnostic according to FIG. 7. It may be understood that both obtaining baseline comparator data and conducting the engine system diagnostic may comprise substantially equivalent methodology, encompassed by method 700.

Accordingly, turning now to FIG. 7, a high level example method 700 for obtaining baseline comparator data and/or conducting the engine system diagnostic, is shown. More specifically, method 700 may be utilized to obtain baseline comparator data that may be used in conjunction with method 600 depicted at FIG. 6, in order to conduct the engine system diagnostic that relies on the baseline comparator data (and where conducting the engine system diagnostic also includes running method 700). In this way, a source of degradation may be pinpointed as to stemming from an intake manifold, an exhaust system, or an engine of a vehicle. Discussed herein, baseline comparator data may include measurements of air flow in the intake as measured by the MAF sensor (e.g. 210) with the engine being spun unfueled in forward direction, and then the reverse direction, and measurements of air flow in the exhaust system as measured by the differential pressure sensor (e.g. 263) with the engine being spun unfueled in the forward direction, and in some examples, with the engine being spun unfueled in the reverse direction. Similarly, "conducting the engine system diagnostic" may also include obtaining measurements of air flow in the intake where the engine is spun unfueled in the forward and then reverse direction, and measurements of air flow in the exhaust system where the engine is spun unfueled in the forward direction, and in some examples, with the engine being spun unfueled in the reverse direction. It may be understood that, while the engine is being spun in the forward direction, both the measurements of air flow in the intake and measurements of air flow in the exhaust system, may be determined, and vice versa.

Method 700 will be described with reference to the systems described herein and shown in FIGS. 1-5B, though it should be understood that similar methods may be applied to other systems without departing from the scope of this disclosure. Method 700 may be carried out by a controller, such as controller 212 in FIG. 2, and may be stored at the controller as executable instructions in non-transitory memory. Instructions for carrying out method 700 and the rest of the methods included herein may be executed by the controller based on instructions stored on a memory of the controller and in conjunction with signals received from sensors of the engine system, such as the sensors described above with reference to FIGS. 1-4. The controller may employ engine system actuators, such as motor (e.g. 120), throttle (e.g. 262), canister purge valve (e.g. 261), etc., according to the method below.

As discussed, method 700 may be conducted to obtain baseline comparator data, and subsequently, method 700 may be utilized to conduct the engine system diagnostic, where the engine system diagnostic utilizes the baseline comparator data to determine whether there is degradation stemming from the intake manifold, exhaust system, or engine of the vehicle. Thus, method 700 will be described initially as being utilized for obtaining baseline comparator data. Subsequently, it will be discussed as to how method 700 may be used to conduct the engine system diagnostic.

Method 700 begins at 705 and may include controlling a throttle (e.g. 262) to a predetermined throttle position. As discussed above, such a throttle may comprise an electronic throttle, which may be actuated to open or close via the vehicle controller, using power supplied from an onboard energy storage device (e.g. 150), which may include a battery, for example. The predetermined throttle position may comprise a position that is more open than a closed position, for example, to allow intake air to be drawn into the engine via the intake manifold when the engine is spun in the forward direction, and/or to allow for air to be pushed to atmosphere via the intake when the engine is spun in the reverse direction (e.g. atmospheric air may be drawn into the engine via the exhaust system, and pushed to atmosphere via the intake manifold and intake of the engine). For example, the throttle may be actuated to fully open, or to some fraction (e.g. 75%, 60%, 50%, 40%, 30%, 20%, etc.) of fully open.

Responsive to controlling the throttle to the predetermined throttle position, method 700 may proceed to 710. At 710, method 700 may include rotating or spinning the engine unfueled for a predetermined duration at a predetermined speed (e.g. predetermined RPM). The predetermined duration may comprise a duration whereby robust measurements of air flow may be obtained via the MAF sensor (e.g. 210), and via the differential pressure sensor (e.g. 263). Rotating the engine unfueled may comprise rotating the engine in the same direction as when the engine is operated to combust air and fuel. In other words, rotating the engine unfueled may comprise rotating the engine in a forward or default direction. Rotating the engine unfueled in the forward direction may comprise routing air flow through the intake of the engine, intake manifold of the engine, the engine, and the exhaust system of the engine, in that order. Rotating the engine unfueled may further comprise rotating the engine via the motor (e.g. 120), where the motor may be powered via the onboard energy storage device (e.g. 150), such as a battery. The speed of the engine may be further controlled via the motor, to the predetermined speed. The predetermined engine speed may comprise a speed at which robust measurements of air flow may be obtained via the MAF sensor (e.g. 210), and via the differential pressure sensor (e.g. 263). Furthermore, while not explicitly illustrated, it may be understood that a canister purge valve (e.g. 261) may be maintained closed during the spinning the engine, in order to ensure that air is not drawn from the evaporative emissions system and/or fuel system. Still further, while not explicitly shown, for vehicles equipped with exhaust gas recirculation (EGR) (e.g. high pressure EGR and/or low pressure EGR), one or more valve(s) controlling exhaust gas recirculation may be commanded or maintained closed.

Even further, for rotating the engine unfueled, valve timing may be controlled to default values.

With the engine being spun unfueled at the predetermined engine speed for the predetermined duration, method 700 may proceed to 715. At 715, method 700 may include obtaining measurements of air flow in the intake and measurements of air flow in the exhaust system. More specifically, the MAF sensor (e.g. 210) may be used at step 720 to obtain a first baseline intake air flow measurement(s), while the differential pressure sensor (e.g. 263) may be used at step 725 to obtain a first baseline exhaust air flow measurement(s). Such measurements may be obtained by taking one or more individual measurements over the predetermined duration that the engine is being spun unfueled. In an example where more than one measurement is obtained while the engine is being spun unfueled, such measurements may be averaged or otherwise processed to obtain a high confidence value for the desired measurements.

Such obtained measurements may be stored at the vehicle controller, for use in conducting the engine system diagnostic, discussed in further detail below and at FIG. 6.

Responsive to obtaining the first baseline intake air flow measurements and the first baseline exhaust air flow measurements at steps 720 and 725, respectively, method 700 may proceed to 730. At 730, method 700 may include stopping spinning the engine unfueled in the forward direction, and may further comprise maintaining the throttle in its current configuration. For example, the motor (e.g. 120) may be commanded to bring the engine to a stop, while the vehicle controller may send a signal to the electronic throttle, commanding or maintaining the throttle to its current position.

In response to an indication that the engine has spun to rest, method 700 may proceed to 735. At 735, method 700 may include rotating or spinning the engine unfueled for a predetermined duration at a predetermined speed (e.g. predetermined RPM), in the reverse direction. Rotating the engine unfueled may comprise rotating the engine in the opposite direction as when the engine is operated to combust air and fuel, and in the opposite direction as the forward engine spin depicted at step 710 of method 700. Rotating the engine unfueled in the reverse direction may include routing air flow through the exhaust system, the engine, the intake manifold, and the intake, in that order. In some examples, the predetermined duration and the predetermined speed of engine rotation may be the same duration and speed as that indicated above at step 710 of method 700. However, in other examples, the predetermined duration and the predetermined speed may be different when spinning or rotating the engine in the reverse direction, as compared to the forward direction. Similar to that discussed above for rotating the engine in the forward direction, rotating the engine unfueled in the reverse direction may comprise rotating the engine via the motor (e.g. 120), where the motor may be powered via the onboard energy storage device (e.g. 150), such as a battery. To rotate the engine in reverse, an H-bridge circuit, such as that depicted at FIGS. 5A-5B, may be utilized. The speed of the engine may be controlled via the motor, to the predetermined speed. Similar to that described above, the predetermined engine speed may comprise a speed at which robust measurements of air flow may be obtained via the MAF sensor (e.g. 210) while the engine is being spun in reverse. Furthermore, while not explicitly illustrated, it may be understood that the canister purge valve (e.g. 261) may be maintained closed during the spinning the engine, in order to ensure that air is not routed to the evaporative emissions system and/or fuel system. Still further, while not explicitly shown, for vehicles equipped with exhaust gas recirculation (EGR) (e.g. high pressure EGR and/or low pressure EGR), one or more valve(s) controlling exhaust gas recirculation may be commanded or maintained closed. Even further, for rotating the engine unfueled in the reverse direction, valve timing may be controlled to default values.

With the engine being spun unfueled in the reverse direction at the predetermined engine speed, method 700 may proceed to 740. At 740, method 700 may include obtaining measurements of air flow in the intake. More specifically, the MAF sensor (e.g. 210) may be used at step 740 to obtain a second baseline intake air flow measurement(s). Such measurements may be obtained by taking one or more individual measurements over the predetermined duration that the engine is being spun unfueled in the reverse direction. In an example where more than one measurement is obtained while the engine is being spun unfueled, such measurements may be averaged or otherwise processed to obtain a high confidence value for the desired measurements.

Such obtained measurements may be stored at the vehicle controller, for use in conducting the engine system diagnostic, discussed in further detail at FIG. 6.

Responsive to obtaining the second baseline intake air flow measurements while the engine is being spun in reverse, method 700 may proceed to 745. At 745, method 700 may include stopping spinning the engine unfueled in the reverse direction, and may further comprise returning the throttle to a default position or configuration. For example, the motor (e.g. 120) may be commanded via the controller to bring the engine to a stop, while the vehicle controller may send a signal to the electronic throttle, actuating the throttle to a default position.

As mentioned above, it may be understood that the methodology discussed at FIG. 7 pertains to both obtaining the baseline comparator data, as well as to conducting the engine system diagnostic subsequent to obtaining the baseline comparator data. As such, the methodology will not be reiterated for brevity. Thus, it may be understood that the entirety of method 700 may be used in conjunction with FIG. 6 to obtain baseline comparator data at step 610, as well as to conduct the engine system diagnostic at step 625.

More specifically, as discussed, method 700 may be used to first obtain baseline comparator data, and may then subsequently be used to conduct the engine system diagnostic. Thus, if method 700 is used to obtain baseline comparator data, it may be understood that at step 720, method 700 may include obtaining the first baseline intake air flow, and step 725 may include obtaining the first baseline exhaust air flow. Furthermore, at step 740, method 700 may include obtaining second baseline intake air flow. Alternatively, if method 700 is used to conduct the engine system diagnostic, then at step 720 method 700 may include obtaining a first intake air flow, and step 725 may include obtaining a first exhaust air flow. Furthermore, at step 740, method 700 may include obtaining a second intake air flow. Discussed herein, obtaining the first intake air flow and the first exhaust air flow may comprise a first condition, and obtaining the second intake air flow may comprise a second condition. Additionally, obtaining the first baseline intake air flow and obtaining the first baseline exhaust air flow may comprise a third condition, and obtaining the second baseline intake air flow may comprise a fourth condition. Thus, the first condition and the third condition includes spinning the engine in the forward direction, while the second condition and fourth condition includes spinning the engine in the reverse direction.

Accordingly, returning to step 625 of method 600, responsive to an indication that baseline comparator data has been obtained, and that conditions are met for conducting an engine system diagnostic, method 600 may include obtaining the intake flow measurements under both forward and reverse engine spinning, and obtaining the exhaust flow measurements under forward engine spinning, and in some examples during reverse engine spinning, as discussed with regard to FIG. 7. Responsive to such measurements being obtained at 625, method 600 may proceed to 630. At step 630, method 600 may include interpreting the results of the engine system diagnostic conducted at step 625, according to FIG. 8.

Thus, proceeding to FIG. 8, it illustrates an example lookup table that may be utilized to interpret the results of the engine system diagnostic. Such a lookup table may be stored at the vehicle controller, for example. As illustrated at FIG. 8, there may be four distinct outcomes (A-D) that may result from the engine system diagnostic.

Outcome A may include a situation where the measurement of intake air flow as measured by the MAF sensor is substantially equivalent to the baseline measurement of intake air flow as measured by the MAF sensor, but where exhaust flow as monitored by the differential pressure sensor is greater than the baseline measurement of exhaust flow as measured by the differential pressure sensor, under conditions where the engine is spun unfueled in the forward direction. In such an example, it may be indicated that there is a source of degradation stemming from the intake manifold, such as that depicted above at FIG. 3A. As discussed, a source of degradation stemming from the intake manifold may result in unmetered air being introduced into the engine, and as such, air flow in the exhaust system may be greater than that expected under conditions where no sources of degradation are present (e.g. under baseline conditions).

Outcome A may additionally or alternatively include a situation where measurements of intake air flow as measured by the MAF sensor while spinning the engine unfueled in the forward direction are substantially equivalent to the baseline measurements of intake air flow obtained during spinning the engine in the forward direction (see steps 710-725 of method 700), but where measurements of intake air flow as measured by the MAF sensor while spinning the engine unfueled in reverse are less than the baseline measurements of intake air flow obtained during spinning the engine in the reverse direction. In other words, such a method of inferring whether there is degradation stemming from the intake manifold may be conducted in some examples in a vehicle that does not include a differential pressure sensor (e.g. 263). For example, because indicating whether there is a source of degradation involves MAF sensor data under conditions where the engine is spun in a forward direction, and then a reverse direction, but may not involve differential pressure sensor data, then such a determination of intake manifold degradation may in some examples be conducted in the absence of such differential pressure sensor data, which may in some examples include an absence of a differential pressure sensor in the exhaust system.

Outcome B may include a situation where the measurement of intake air flow as measured by the MAF sensor during spinning the engine unfueled in the forward direction is substantially equivalent to the baseline measurement of intake air flow as measured by the MAF sensor during spinning the engine unfueled in the forward direction, but where exhaust flow as monitored by the differential pressure sensor is less than the baseline measurement of exhaust flow as measured by the differential pressure sensor, under conditions of spinning the engine unfueled in the forward direction. In such an example, it may be indicated that there is a source of degradation stemming from the exhaust system, such as that depicted above at FIG. 3B. As discussed, a source of degradation stemming from the exhaust system may thus result in exhaust flow being forced to atmosphere via the source of degradation, prior to reaching the differential pressure sensor, when the engine is spun unfueled in the forward direction. Accordingly, such a process may result in a differential pressure sensor reading below that expected under conditions where no sources of degradation are present (e.g. under baseline conditions).

Outcome B may additionally or alternatively include a situation where the measurement of intake air flow as measured by the MAF sensor during spinning the engine unfueled in the forward direction is substantially equivalent to the baseline measurement of air flow in the intake, but where the measurement of intake air flow as measured by the MAF sensor during spinning the engine unfueled in the reverse direction is greater than the baseline measurement of air flow in the intake under similar conditions. In such an example, it may be understood that degradation in the exhaust system may result in additional air being drawn into the engine via the source of degradation in the exhaust system, and pushed through the engine to the intake, under conditions of spinning the engine unfueled in reverse.

Outcome C may include a situation where both air flow in the intake as measured by the MAF sensor during spinning the engine unfueled in the forward direction, as well as air flow in the exhaust as measured by the differential pressure sensor during spinning the engine unfueled in the forward direction, are less than baseline measurements obtained via the MAF sensor and the differential pressure sensor under conditions of spinning the engine unfueled in the forward direction. In such an example, it may be understood that there may be a source of degradation stemming from the engine compartment related to engine operation. As discussed, such a source of degradation may comprise intake and/or exhaust valves that are not sealing properly, compression issues related to engine cylinder(s), degraded piston rings, degraded head gasket, undesired camshaft timing, etc. In such a case where the engine is identified as the source of degradation, the engine may not pump as expected, thus resulting in overall less air drawn into the engine via the intake manifold, and a corresponding lower amount of exhaust flow routed through the exhaust system.

Outcome C may additionally or alternatively include a situation where intake air flow as measured by the MAF sensor under conditions where the engine is spun unfueled in the forward direction is less than the baseline MAF sensor data obtained under conditions where the engine is spun unfueled in the forward direction, and where intake air flow is less than the baseline intake air flow under conditions where the engine is being spun unfueled in the reverse direction. In such an example, there may be degradation stemming from the engine compartment, as less overall air is indicated to be being drawn into the intake system when the engine is spun in the forward direction as compared to baseline measurements obtained under similar conditions of forward engine-spinning, and as less overall air is indicated to be being pushed through the intake system when the engine is spun in the reverse direction as compared to baseline measurements obtained under similar conditions of reverse engine-spinning. Thus, it may be understood that such a method of inferring whether there is degradation stemming from the engine compartment may be conducted in some examples in a vehicle that does not include a differential pressure sensor (e.g. 263). For example, because indicating whether there is a source of degradation involves MAF sensor data under conditions where the engine is spun in a forward direction, and then a reverse direction, but does not involve differential pressure sensor data, then such a determination of engine compartment degradation may in some examples be conducted in the absence of such differential pressure sensor data, which may in some examples include an absence of a differential pressure sensor in the exhaust system.

Outcome D may include a situation where both the air flow in the intake as measured by the MAF sensor under conditions where the engine is spun unfueled in the forward direction, as well as air flow in the exhaust system as measured by the differential pressure sensor under conditions where the engine is spun unfueled in the forward direction, are substantially equivalent to baseline measurements made by the MAF sensor and the differential pressure sensor under conditions where the engine is spun unfueled in the forward direction. In such an example, an absence of a source of degradation stemming from the intake manifold, exhaust system, and/or engine may be indicated.

Outcome D may additionally or alternatively include a situation where air flow in the intake as measured by the MAF sensor is substantially equivalent to baseline air flow in the intake under conditions of spinning the engine unfueled in the forward direction, and where air flow in the intake as measured by the MAF sensor is substantially equivalent to baseline air flow in the intake under conditions of spinning the engine unfueled in the reverse direction. Thus, it may be understood that such a method of inferring whether there is an absence of degradation stemming from the intake manifold, engine, or exhaust system may be conducted in some examples in a vehicle that does not include a differential pressure sensor (e.g. 263). For example, because indicating whether there is an absence of degradation involves MAF sensor data under conditions where the engine is spun in a forward direction, and then a reverse direction, but does not involve differential pressure sensor data, then such a determination of the absence of engine system degradation may in some examples be conducted in the absence of such differential pressure sensor data, which may in some examples include an absence of a differential pressure sensor in the exhaust system.

It may be understood that in each of the above-discussed potential outcomes A-D, sensor readings that are substantially equivalent to their respective baseline measurements may comprise measurements being within a certain range of each other, for example less than or equal to a 5% difference in measurements over the span of the engine system diagnostic, or less than or equal to a 5% difference in averaged measurements comprising the span of the engine system diagnostic. Thus, it may be further understood that data less than/greater than baseline data may comprise data greater than a 5% difference from the baseline data.

It may be further understood that there may be circumstances where it may be desirable to conduct the engine system diagnostic or to obtain baseline comparator data by spinning the engine unfueled in the forward direction, but not in the reverse direction, or vice versa. For example, consider a situation where battery power is low or limited, and thus it may not be desirable to spin the engine in both the forward and reverse directions, to conduct the engine system diagnostic. Instead, it may be desirable to only spin the engine unfueled in the forward direction, for example. In such an example, degradation of either the intake, engine compartment, or exhaust system may be effectively diagnosed provided the vehicle includes the MAF sensor and the differential pressure sensor. However, in situations where the vehicle does not include both the MAF sensor and the differential pressure sensor, then the MAF sensor may be utilized to infer the presence or absence of degradation stemming from the intake, engine compartment, or exhaust system, under conditions of forward and reverse engine spinning (for obtaining baseline intake and exhaust flow, and for conducting the engine system diagnostic under similar conditions), as discussed above.

Returning to FIG. 6, subsequent to interpreting the results of the engine system diagnostic at step 630 of method 600, method 600 may proceed to 635. At 635, method 600 may include adjusting vehicle operating parameters according to the results of the engine system diagnostic. As examples, provided that a source of degradation is identified in the intake manifold, exhaust system, and/or engine, a MIL may be illuminated on the vehicle dash alerting the vehicle operator of a request to service the vehicle.

If a source of degradation is indicated as stemming from the intake manifold, the vehicle controller may adjust throttle position in some examples during fueled engine operation, in order to account for the unmetered air entering the engine via the source of degradation.

In other examples, where the source of degradation is indicated as stemming from either the intake manifold, exhaust system, or engine compartment, adjusting vehicle operating parameters may include the vehicle controller commanding an electric mode of operation as frequently as possible, to mitigate a potential release of undesired emissions to atmosphere, and/or to mitigate potential mechanical issues with the engine under circumstances where the engine is ingesting a greater amount of air than desired, or to mitigate issues already present in the engine compartment.

Thus, in one example, a method may include spinning an engine of a vehicle unfueled in a forward and a reverse direction to obtain a first intake air flow and a second intake air flow, respectively, in an intake of the engine. The method may further include indicating a source of degradation stemming from one of the engine, an intake manifold of the engine, or an exhaust system of the engine based on both the first air flow and the second air flow.

In such a method, prior to spinning the engine unfueled in the forward and the reverse direction to obtain the first intake air flow and the second intake air flow, the method may include obtaining a set of baseline comparator data that includes spinning the engine unfueled in the forward and the reverse direction to obtain a first baseline intake air flow and a second baseline intake air flow. It may be understood that spinning the engine unfueled in the forward and reverse direction may be conducted via a motor powered by a battery.

In such a method, obtaining the first baseline intake air flow and the second baseline intake air flow may include spinning the engine in the forward and the reverse direction, respectively, under a substantially equivalent set of conditions as that for obtaining the first intake air flow and the second intake air flow. For example, the substantially equivalent set of conditions may include spinning the engine in the forward direction at a first predetermined speed and for a first predetermined duration of time, spinning the engine in the reverse direction at a second predetermined speed and for a second predetermined duration of time, and controlling a throttle positioned in the intake manifold to a predetermined position during spinning the engine in the forward and reverse directions.

In such a method, obtaining the first intake air flow, the second intake air flow, the first baseline intake air flow, and the second baseline intake air flow may include sealing the intake manifold and the engine from an evaporative emissions system of the vehicle, and sealing the engine, intake manifold, and exhaust system from an exhaust gas recirculation system, configured to recirculate at least a portion of exhaust gas from the engine to the intake manifold under predetermined conditions of engine operation.

In such a method, it may be understood that obtaining the set of baseline comparator data includes conditions where the intake manifold of the engine, the engine, and the exhaust system of the engine are indicated to be free from the source of degradation.

In such a method, the engine, the intake manifold, and the exhaust system are indicated to be free from the source of degradation responsive to the first intake air flow being substantially equivalent to the first baseline intake air flow and the second intake air flow being substantially equivalent to the second baseline intake air flow. Alternatively, the source of degradation may be indicated to be the intake manifold responsive to the first intake air flow being substantially equivalent to the first baseline intake air flow, but where the second intake air flow is less than the second baseline intake air flow. In another example, the source of degradation may be indicated to be the engine responsive to both the first intake air flow being less than the first baseline intake air flow and the second intake air flow being less than the second baseline intake air flow. In still another example, the source of degradation may be indicated to be the exhaust system responsive to the first intake air flow being substantially equivalent to the first baseline intake air flow, but where the second intake air flow is greater than the second baseline intake air flow.

Another example of a method comprises routing a first air flow through an intake of an engine, intake manifold of the engine, the engine, and an exhaust system of the engine, in that order in a first condition; routing a second air flow through the exhaust system, the engine, the intake manifold, and the intake, in that order, in a second condition; indicating a first intake air flow in the first condition and a second intake air flow in the second condition; indicating a first exhaust air flow in the first condition; and diagnosing a presence or an absence of degradation stemming from one of the intake manifold, the engine, or the exhaust system as a function of two or more of the first intake air flow, the second intake air flow, and/or the first exhaust air flow.

In such a method, the method may further comprise in a third condition, indicating a first baseline intake air flow and indicating a first baseline exhaust air flow; in a fourth condition, indicating a second baseline intake air flow. In such an example, the third condition may include routing a third air flow through the intake of the engine, intake manifold of the engine, the engine, and the exhaust system of the engine, in that order, and the fourth condition may include routing a fourth air flow through the exhaust system, the engine, the intake manifold, and the intake, in that order.

In such a method, the first condition and the third condition may include rotating the engine unfueled via a motor in a forward direction to route the first air flow through the intake, the intake manifold, the engine, and the exhaust system, in that order. In such a method, the second condition and the fourth condition may include rotating the engine unfueled via the motor in a reverse direction to route the second air flow through the exhaust system, the engine, the intake manifold, and the intake, in that order.

In such a method, it may be understood that routing the first air flow includes routing the first air flow for a first predetermined duration, and where routing the third air flow includes routing the third air flow for the first predetermined duration. As an example, routing the second air flow may include routing the second air flow for a second predetermined duration, routing the fourth air flow may include routing the fourth air flow for the second predetermined duration, where the first predetermined duration is either the same or different than the second predetermined duration. In such a method, each of the first condition, second condition, third condition, and fourth condition may include controlling a throttle position in the intake of the vehicle to a predetermined open position. In such a method, each of the first condition, second condition, third condition, and fourth condition may include sealing an evaporative emissions system from the intake, intake manifold, engine, and exhaust system, the evaporative emissions system configured to capture and store fuel vapors from a fuel system of the vehicle, and wherein each of the first condition, second condition, third condition, and fourth condition includes sealing the intake, intake manifold, engine, and exhaust system from an exhaust gas recirculation system, the exhaust gas recirculation system configured to route at least a portion of exhaust gases from the engine to the intake manifold.

In such a method, the method may further comprise indicating the presence of degradation stemming from the intake manifold responsive to the first intake air flow being substantially equivalent to the first baseline intake air flow and where the first exhaust air flow is greater than the first baseline exhaust air flow, and/or where the first intake air flow is substantially equivalent to the first baseline intake air flow and where the second intake air flow is less than the second baseline intake air flow. Alternatively, the method may include indicating the presence of degradation stemming from the exhaust system responsive to the first intake air flow being substantially equivalent to the first baseline intake air flow and where the first exhaust air flow is less than the first baseline exhaust air flow, and/or where the first intake air flow is substantially equivalent to the first baseline intake air flow and where the second intake air flow is greater than the second baseline intake air flow. In still another example, the method may include indicating the presence of degradation stemming from the engine responsive to the first intake air flow being less than the first baseline intake air flow and responsive to the first exhaust air flow being less than the first baseline exhaust air flow, and/or where the first intake air flow is less than the first baseline intake air flow and where the second intake air flow is less than the second baseline intake air flow.

In such a method, it may be understood that the third condition and the fourth condition may be conducted under conditions where degradation in the intake manifold, engine and exhaust system is not already indicated. It may be further understood that the first condition, second condition, third condition, and fourth condition may all be conducted under conditions where the vehicle is not occupied and where the vehicle is not in motion. It may be further understood that the first intake air flow, the first baseline intake air flow, the second intake air flow, and the second baseline intake air flow may be indicated via a mass air flow sensor positioned in the intake manifold of the engine, and where the first exhaust air flow and the first baseline exhaust air flow are indicated via a differential pressure sensor positioned in the exhaust system.

Turning now to FIG. 9, an example timeline 900 is shown for obtaining baseline comparator measurements, as well as conducting an engine system diagnostic in a vehicle, according to the methods depicted herein and with reference to FIGS. 6-8, and as applied to the systems depicted herein and with reference to FIGS. 1-5B. Timeline 900 includes plot 905, indicating whether an engine off, or is on and spinning in a forward (fwd) or reverse (rev) direction, over time. Timeline 900 further includes plot 910, indicating whether fuel injection to one or more engine cylinders, is on, or off, over time. Timeline 900 further includes plot 915, indicating whether a throttle (e.g. 262) is open, closed, or some level between open and closed (e.g. some fraction of fully open). Timeline 900 further includes plot 920, indicating an engine speed (RPM), over time. Engine speed may be either 0 (fully stopped), or may be greater (+) than fully stopped. Timeline 900 further includes plot 925, indicating air flow in the intake of the vehicle, as monitored by the MAF sensor (e.g. 210). The MAF sensor may indicate an absence of air flow (0), or may indicate air flow greater (+) than the absence of air flow. It may be understood that air flow may either be air flow to the engine (engine spinning in the forward direction) from the intake, or air flow from the engine and exhaust system to the intake (engine spinning in the reverse direction).

Timeline 900 further includes plot 930, indicating air flow in the exhaust system of the vehicle, as monitored by the differential pressure sensor (e.g. 263). The differential pressure sensor may indicate an absence of air flow (0), or may indicate air flow greater (+) than the absence of air flow. It may be understood that air flow in the exhaust system may either comprise air flow from the engine to the exhaust system (engine spinning in the forward direction) or air flow to the engine from the exhaust system (engine spinning in the reverse direction). Timeline 900 further includes plot 935, indicating an air-fuel ratio as monitored via an exhaust gas sensor (e.g. 237), over time. Air-fuel ratio may be either stoichiometric (ideal ratio of air to fuel that burns all fuel with no excess air), or may be either rich or lean of stoichiometry.

Timeline 900 further includes plot 940, indicating whether conditions are indicated to be met for obtaining baseline comparator data, plot 945, indicating whether conditions are indicated to be met for conducting the engine system diagnostic, plot 950, indicating whether the vehicle is occupied, and plot 955, indicating whether a source of degradation is present in the engine system, over time. The source may be the engine, intake manifold (intake) or exhaust system (exhaust).

At time t0, the engine is off (plot 905), and accordingly, fuel is not being injected into engine cylinders (plot 910), and engine speed is 0 RPM (plot 920). While not explicitly shown, it may be understood that at time t0, the vehicle is also not being propelled via a motor. A position of the throttle is substantially closed, reflecting a position of the throttle in an engine off/vehicle off state. With the engine off, there is no air-fuel ratio to measure, and thus an air-fuel ratio is not indicated at time t0. Similarly, a MAF sensor positioned in an intake manifold downstream of the throttle is not registering any air flow (plot 925) in the intake, and the differential pressure sensor is also not registering any air flow in the exhaust system (plot 930). At time t0, conditions are not indicated to be met for obtaining baseline comparator data (plot 940), and conditions are further not indicated to be met for conducting an engine system diagnostic test (plot 945). The vehicle is not indicated to be occupied (plot 950), and degradation is not indicated in the engine system (plot 955).

At time t1, conditions are indicated to be met for obtaining baseline comparator data (plot 940). Conditions being met for obtaining baseline comparator data have been discussed with regard to step 605 of method 600, and for brevity, will not be reiterated here. However, it may be understood that in this example timeline 900, conditions being met may include a situation where a predetermined duration of time has elapsed since a key-off event, where the controller is woken up in order to obtain the baseline comparator data. With conditions being met for obtaining baseline comparator data, the engine may be activated to be spun in a forward (or default) direction. More specifically, the vehicle controller may command the motor (e.g. 120) to rotate the engine unfueled in the forward or default direction. As such, fuel injection to the cylinders of the engine may be maintained off (plot 910). The motor may control engine speed to a predetermined engine speed (plot 920). Furthermore, the throttle may be controlled to a predetermined throttle position (plot 915), as discussed above with regard to step 705 of method 700 depicted at FIG. 7.

The time period between time t1 and t2 may comprise a predetermined time period for spinning the engine in the forward direction unfueled. By spinning the engine unfueled in the forward direction, air may be drawn through the intake and into the engine, before being routed to the exhaust system. As fuel injection (and spark) is not being provided to the engine cylinders, the air-fuel ratio indicates a lean condition (plot 935), as indicated by the exhaust gas sensor (e.g. 237). Air flow in the intake is monitored by the MAF sensor between time t1 and t2 (plot 925), and air flow in the exhaust system is monitored via the differential pressure sensor (plot 930). As discussed, such measurements may be stored at the controller of the vehicle, such that subsequent measurements of air flow in the intake and subsequent measurements of air flow in the exhaust system may be compared to the baseline measurements. In this way, potential sources of degradation stemming from the intake manifold, exhaust system, or engine, may be pinpointed.

Subsequent to the predetermined time duration of spinning the engine unfueled in the forward direction elapsing, the engine is controlled via the electric motor to 0 RPM. In other words, the engine is spun to rest between time t2 and t3. However, the throttle is maintained in its current state, in order to avoid the throttle being closed, then opened again in order to spin the engine in the reverse direction.

Between time t2 and t3, with the engine spinning to rest, air flow in the intake (plot 925) and air flow in the exhaust system (plot 930) returns to 0, or no flow. After the engine is spun to rest, at time t3, the engine is controlled to spin unfueled in the reverse direction. As discussed an H-bridge circuit such as that depicted at FIGS. 5A-5B may be utilized to enable the motor to spin the engine unfueled in the reverse direction.

The time period between time t3 and t4 may comprise a predetermined time period for spinning the engine in the reverse direction unfueled. By spinning the engine unfueled in the reverse direction, air may be drawn through the exhaust system and into the engine, before being routed out of the engine to engine intake. As air is drawn across the exhaust gas sensor, a lean condition is indicated (plot 935). Air flow in the intake is monitored by the MAF sensor between time t3 and t4 (plot 925), and air flow in the exhaust system is monitored via the differential pressure sensor (plot 930). As discussed, such measurements may be stored at the controller of the vehicle, such that subsequent measurements of air flow in the intake and subsequent measurements of air flow in the exhaust system may be compared to the baseline measurements. In this way, potential sources of degradation stemming from the intake manifold, exhaust system, or engine, may be pinpointed, as discussed above and which will be discussed further below.

Subsequent to the predetermined time duration of spinning the engine unfueled in the reverse direction elapsing, the engine is controlled via the electric motor to 0 RPM. In other words, the engine is spun to rest between time t4 and t5. Furthermore, the throttle is actuated via the controller to a default configuration, which in this example includes a configuration that the throttle was at prior to obtaining the baseline comparator data. With the engine being spun to rest between time t4 and t5, air flow decreases to no flow in the intake as measured by the MAF sensor, and air flow in the exhaust system decreases to no flow as measured by the differential pressure sensor. As baseline comparator data has been obtained for both conditions of spinning the engine unfueled in the forward and reverse directions, and stored at the controller, and with the predetermined time duration elapsing at time t4, conditions are no longer indicated to be met for obtaining the baseline comparator data.

At time t5, the vehicle becomes occupied (plot 950). Such an indication may be provided via door sensors, seat load cells, onboard camera(s), etc. Furthermore, the engine is turned on (plot 905), with fuel injection provided to one or more engine cylinders (plot 910). In other words, at time t5, a vehicle operator has entered the vehicle and started the engine, with the intent to drive the vehicle. With fuel injection provided to the engine cylinders, it may be understood that the engine is operating in the forward direction, indicated at plot 905.

Between time t5 and t6, the vehicle is driven, and accordingly throttle position (plot 915) varies as a function of driver demand, and engine speed (plot 920) is controlled as a function of driver demand. With the engine in operation, both the MAF sensor (plot 925) and the differential pressure sensor (plot 930) measure intake air flow, and exhaust flow, respectively, which vary as a function of driver demand.

Between time t5 and t6, air-fuel ratio is maintained substantially equivalent to stoichiometric air-fuel ratio. However, at time t6, the air-fuel ratio switches lean. As discussed above, a change in air-fuel ratio may be indicative of potential degradation in the engine system. Thus, it may be understood that, in response to the change in air-fuel ratio indicated at time t6, such a result may be stored at the vehicle controller, such that an engine system diagnostic may be initiated at the next opportunity where conditions are indicated to be met for conducting the engine system diagnostic.

Between time t6 and t7, the vehicle is continued to be operated with the engine combusting air and fuel. In some examples, responsive to a disturbance in air-fuel ratio, adaptive fuel learning may correct the lean air-fuel ratio, indicated by dashed line 936. However, in other examples, the vehicle may not include adaptive fuel learning.

At time t7, the engine is turned off (plot 905), and fueling to the engine is stopped (plot 910). Furthermore, at time t7, the vehicle once again becomes unoccupied (plot 950).

After some time, at time t8, conditions are indicated to be met for conducting the engine system diagnostic as discussed above with regard to step 615 of method 600. For brevity, such conditions will not be reiterated here. However, it may be understood in this example timeline 900, conditions being met may include a situation where a predetermined duration of time has elapsed since a key-off event, where the controller is woken up in order to conduct the engine system diagnostic. Accordingly, with conditions being met for conducting the engine system diagnostic, the engine is activated to be spun in a forward or default direction at time t8. More specifically, the vehicle controller may command the motor (e.g. 120) to rotate the engine unfueled in the forward or default direction. As such, fuel injection to the cylinders of the engine may be maintained off (plot 910). The motor may control engine speed (plot 920) to the same engine speed as engine speed during obtaining the baseline comparator data (e.g. engine speed between time t1 and t2). Furthermore, the throttle may be controlled to the same predetermined throttle position, as the throttle position during obtaining the baseline comparator data (e.g. throttle position between time t1 and t2).

The time period between time t8 and t9 may comprise the predetermined time period for spinning the engine unfueled in the forward direction unfueled to conduct the engine system diagnostic. More specifically, the predetermined time period for spinning the engine in the forward direction unfueled to conduct the engine system diagnostic may comprise the same predetermined time period for spinning the engine unfueled in the forward direction to obtain the baseline comparator data (e.g. between time t1 and t2). As discussed, by spinning the engine unfueled in the forward direction, air may be drawn through the intake and into the engine, before being routed to the exhaust system. As fuel injection (and spark) is not being provided to the engine cylinders, the air-fuel ratio indicates a lean condition (plot 935), as indicated by the exhaust gas sensor (e.g. 237). Air flow in the intake is monitored by the MAF sensor between time t8 and t9 (plot 925), and air flow in the exhaust system is monitored via the differential pressure sensor (plot 930). As discussed, such measurements may be stored at the controller of the vehicle, such that the measurements of air flow in the intake and exhaust system obtained during conducting the engine diagnostic by spinning the engine unfueled in the forward direction may be compared to the baseline measurements obtained under the same conditions. In this way, potential sources of degradation stemming from the intake manifold, exhaust system, or engine, may be pinpointed.

Subsequent to the predetermined time duration of spinning the engine unfueled in the forward direction elapsing, the engine is controlled via the electric motor to 0 RPM. In other words, the engine is spun to rest between time t9 and t10. However, the throttle is maintained in its current state, in order to avoid the throttle being closed, then opened again in order to spin the engine in the reverse direction for conducting the engine system diagnostic.

Between time t9 and t10, with the engine spinning to rest, air flow in the intake (plot 925) and air flow in the exhaust system (plot 930) returns to 0, or no flow. After the engine is spun to rest, at time t10, the engine is controlled to spin unfueled in the reverse direction. As discussed above, an H-bridge circuit such as that depicted at FIGS. 5A-5B may be utilized to enable the motor to spin the engine unfueled in the reverse direction.

The time period between time t10 and t11 may comprise the predetermined time period for spinning the engine in the reverse direction unfueled for conducting the engine system diagnostic. It may be understood that the predetermined time period for spinning the engine in the reverse direction for conducting the engine system diagnostic may comprise the same predetermined duration of spinning the engine unfueled in the reverse direction to obtain the baseline comparator data. By spinning the engine unfueled in the reverse direction, air may be drawn through the exhaust system and into the engine, before being routed out of the engine to engine intake. As air is drawn across the exhaust gas sensor, a lean condition is indicated (plot 935). Air flow in the intake is monitored by the MAF sensor between time t11 and t12 (plot 925), and air flow in the exhaust system is monitored via the differential pressure sensor (plot 930). As discussed, such measurements may be stored at the controller of the vehicle, for comparison to baseline measurements of air flow in the intake and air flow in the exhaust system under similar conditions.

With the predetermined time duration of spinning the engine unfueled in the reverse direction elapsing, conditions are no longer indicated to be met for conducting the engine system diagnostic (plot 945). Accordingly, at time t11, the data acquired between time t8 and t9 related to air flow in the intake is compared to data acquired between time t1 and t2. Furthermore, the data acquired between time t10 and t11 is compared to data acquired between time t3 and t4. As discussed, a lookup table, such as lookup table 800 depicted at FIG. 8 may be utilized to diagnose the presence or absence of degradation in the engine system. More specifically, the data acquired between time t1 and t2 comprises baseline comparator data regarding air flow in the intake and exhaust system while the engine is spun unfueled in the forward direction. Such baseline comparator data may comprise an averaged or otherwise processed first MAF baseline, or first intake air flow baseline, represented by line 926, and an averaged or otherwise processed first differential pressure sensor baseline, or first exhaust flow baseline, represented by line 931. Similarly, the data acquired between time t3 and t4 comprises baseline comparator data regarding air flow in the intake and exhaust system while the engine is spun unfueled in the reverse direction. Such baseline comparator data may comprise an averaged or otherwise processed second MAF baseline, or second intake flow baseline, represented by line 927. While not explicitly illustrated, an averaged or otherwise processed second differential pressure sensor baseline, or second exhaust flow baseline, may in some examples be generated via the controller.

As illustrated, the air flow in the intake (plot 925) acquired during the engine system diagnostic where the engine was spun unfueled in the forward direction (between time t8 and t9) is substantially equivalent to the first intake air flow baseline, represented by line 926. However, the air flow in the intake acquired during the engine system diagnostic where the engine was spun unfueled in the reverse direction (between time t10 and t11) is lower than the second intake air flow baseline, represented by line 927. Turning to FIG. 8, outcome A depicts a situation where intake air flow is substantially equivalent to baseline intake air flow when the engine is spun in the forward direction, but where intake air flow is less than the baseline when the engine is spun in the reverse direction. Accordingly, at time t11, degradation of the intake manifold is indicated (plot 955). The data from air flow in the exhaust system obtained during spinning the engine in the forward direction supports such an indication. Specifically, air flow in the intake (plot 925) acquired during the engine system diagnostic where the engine was spun unfueled in the forward direction (between time t8 and t9) is substantially equivalent to the first intake air flow baseline, represented by line 926. However, the air flow in the exhaust system (plot 930) acquired during the engine system diagnostic where the engine was spun unfueled in the forward direction (between time t8 and t9) is greater than the first exhaust flow baseline, represented by line 931. Turning to FIG. 8, outcome A depicts a situation where intake air flow is substantially equivalent to baseline intake air flow when the engine is spun unfueled in the forward direction, but where air flow in the exhaust is greater than baseline exhaust flow under the same conditions.

Thus, at time t11, degradation is indicated in the intake manifold (plot 955), and with conditions for conducting the engine system diagnostic no longer indicated to be met (plot 945), the engine is deactivated (plot 905), and the motor spins the engine to rest between time t11 and t12. Furthermore, throttle position (plot 915) may be controlled or actuated via the controller to its default configuration. As the engine is spinning to rest between time t11 and t12, engine speed goes to 0 RPM (plot 920), air flow in the intake goes to no flow (plot 925), and air flow in the exhaust system goes to no flow (plot 930). Subsequent to time t12 the engine is maintained off and the vehicle remains unoccupied. While not explicitly shown, the vehicle controller may be put to sleep responsive to conducting the engine system diagnostic.

While not explicitly discussed, it may be understood that in some examples, data acquired related to exhaust flow during spinning the engine unfueled in reverse, may be acquired to obtain baseline exhaust flow while spinning the engine unfueled in reverse, and may additionally be acquired to obtain exhaust flow while spinning the engine unfueled in reverse to conduct the engine system diagnostic. For example, consider a situation where air flow in the exhaust system during spinning the engine unfueled in the forward direction is greater than baseline air flow in the exhaust system acquired under the same circumstances, and where air flow in the exhaust system during spinning the engine unfueled in the reverse direction is substantially equivalent to baseline air flow in the exhaust system acquired under the same circumstances. Such an indication may be indicative of degradation in the intake manifold. In another example, consider a situation where air flow in the exhaust system obtained during both spinning the engine unfueled in the forward direction, and the reverse direction, is lower than baseline data obtained under the same conditions. In such an example, such an indication may be indicative of degradation in the engine system compartment. In still another example, consider a situation where air flow in the exhaust system obtained during spinning the engine unfueled in the forward direction is less than baseline air flow in the exhaust system obtained under similar circumstances, and where air flow in the exhaust system obtained during spinning the engine unfueled in the reverse direction is substantially equivalent to baseline air flow in the exhaust system obtained under similar circumstances. In such an example, such an indication may be indicative of degradation in the exhaust system.

In this way, degradation stemming from one of the intake manifold, exhaust system (upstream of the differential pressure sensor and downstream of the engine), or engine of the engine system may be pinpointed by making use of intake air flow measurements and exhaust flow measurements, in comparison to baseline intake air flow and baseline exhaust flow measurements, where the baseline intake air flow and exhaust flow measurements are obtained under conditions where the engine system is free from degradation. By pinpointing the source of degradation, customer satisfaction may be improved, as time spent working on the vehicle via a technician may be reduced. Furthermore, pinpointing the source of degradation may result in a reduction of release of undesired emissions to atmosphere.

The technical effect is to recognize that a mass air flow sensor positioned in the intake of an engine may be utilized to effectively diagnose degradation in the intake of a vehicle, by monitoring air flow in the intake under conditions where the engine is spun unfueled in the forward direction, and then the reverse direction (or vice versa), and comparing the air flow to baseline air flow under similar conditions of forward and reverse engine spinning. A further technical effect is to recognize that degradation of the exhaust system and/or engine compartment may be indicated in similar fashion by monitoring air flow in the intake under conditions of spinning the engine unfueled in the forward and reverse directions.

Another technical effect is to recognize that an engine system diagnostic may in some examples be conducted by only spinning the engine in the forward direction, and monitoring air flow in the intake and air flow in the exhaust system, and comparing said air flow to baseline air flow in the intake and exhaust system, under similar conditions. For example, it is recognized that a mass air flow sensor positioned in the intake manifold of an engine may not be able to effectively diagnose a source of degradation stemming from the intake manifold by spinning the engine in a forward direction, unless such a measurement of mass air flow is considered in conjunction with a pressure sensor or other sensor to monitor air flow in the exhaust system. Similarly, a source of degradation stemming from an engine, or exhaust system may not be directly inferable under conditions where the engine is spun in the forward direction (but not the reverse direction) unless measurements of intake air flow and exhaust flow are considered together. Thus, a technical effect is to recognize that in some examples, an engine system diagnostic may be conducted by spinning the engine unfueled in the forward direction, but not in the reverse direction, which may be desirable in situations where battery power is low or limited. In all examples (e.g. source of degradation stemming from the intake manifold, exhaust system, or engine), a further technical effect is to recognize that measurements of intake air flow and exhaust flow may be compared to baseline measurements of intake air flow and exhaust flow obtained under similar conditions, such that by comparing both intake air flow and exhaust flow to baseline intake air flow and exhaust flow measurements, respectively, a determination of a source of degradation may be indicated. In this way, a source of degradation stemming from the intake manifold, exhaust system, or engine may be conclusively diagnosed.

The systems described herein, and with reference to FIGS. 1-5B, along with the methods described herein, and with reference to FIGS. 6-7 may enable one or more systems and one or more methods. In one example, a method comprises spinning an engine of a vehicle unfueled in a forward and a reverse direction to obtain a first intake air flow and a second intake air flow, respectively, in an intake of the engine; and indicating a source of degradation stemming from one of the engine, an intake manifold of the engine, or an exhaust system of the engine based on both the first air flow and the second air flow. In a first example of the method, the method further comprises prior to spinning the engine unfueled in the forward and the reverse direction to obtain the first intake air flow and the second intake air flow, obtaining a set of baseline comparator data that includes spinning the engine unfueled in the forward and the reverse direction to obtain a first baseline intake air flow and a second baseline intake air flow; and wherein spinning the engine unfueled in the forward and the reverse direction is conducted via a motor powered by a battery. A second example of the method optionally includes the first example, and further includes wherein obtaining the first baseline intake air flow and the second baseline intake air flow includes spinning the engine in the forward and the reverse direction, respectively, under a substantially equivalent set of conditions as that for obtaining the first intake air flow and the second intake air flow, where the substantially equivalent set of conditions includes spinning the engine in the forward direction at a first predetermined speed and for a first predetermined duration of time, spinning the engine in the reverse direction at a second predetermined speed and for a second predetermined duration of time, and controlling a throttle positioned in the intake manifold to a predetermined position during spinning the engine in the forward and reverse directions. A third example of the method optionally includes any one or more or each of the first and second examples, and further includes wherein spinning the engine unfueled in the forward and the reverse direction to obtain the first intake air flow, the second intake air flow, the first baseline intake air flow, and the second baseline intake air flow further comprises: sealing the intake manifold and the engine from an evaporative emissions system of the vehicle; and sealing the engine, intake manifold, and exhaust system from an exhaust gas recirculation system, configured to recirculate at least a portion of exhaust gas from the engine to the intake manifold under predetermined conditions of engine operation. A fourth example of the method optionally includes any one or more or each of the first through third examples, and further includes wherein obtaining the set of baseline comparator data is conducted under conditions where the intake manifold of the engine, the engine, and the exhaust system of the engine are indicated to be free from the source of degradation. A fifth example of the method optionally includes any one or more or each of the first through fourth examples, and further includes wherein the engine, the intake manifold, and the exhaust system are indicated to be free from the source of degradation responsive to the first intake air flow being substantially equivalent to the first baseline intake air flow and the second intake air flow being substantially equivalent to the second baseline intake air flow. A sixth example of the method optionally includes any one or more or each of the first through fifth examples, and further includes wherein the source of degradation is indicated to be the intake manifold responsive to the first intake air flow being substantially equivalent to the first baseline intake air flow, but where the second intake air flow is less than the second baseline intake air flow. A seventh example of the method optionally includes any one or more or each of the first through sixth examples, and further includes wherein the source of degradation is indicated to be the engine responsive to both the first intake air flow being less than the first baseline intake air flow and the second intake air flow being less than the second baseline intake air flow. An eighth example of the method optionally includes any one or more or each of the first through seventh examples, and further includes wherein the source of degradation is indicted to be the exhaust system responsive to the first intake air flow being substantially equivalent to the first baseline intake air flow, but where the second intake air flow is greater than the second baseline intake air flow.

Another example of a method comprises routing a first air flow through an intake of an engine, intake manifold of the engine, the engine, and an exhaust system of the engine, in that order in a first condition; routing a second air flow through the exhaust system, the engine, the intake manifold, and the intake, in that order, in a second condition; indicating a first intake air flow in the first condition and a second intake air flow in the second condition; indicating a first exhaust air flow in the first condition; and diagnosing a presence or an absence of degradation stemming from one of the intake manifold, the engine, or the exhaust system as a function of two or more of the first intake air flow, the second intake air flow, and/or the first exhaust air flow. In a first example of the method, the method further comprises in a third condition, indicating a first baseline intake air flow and indicating a first baseline exhaust air flow; in a fourth condition, indicating a second baseline intake air flow; and wherein the third condition includes routing a third air flow through the intake of the engine, intake manifold of the engine, the engine, and the exhaust system of the engine, in that order; and wherein the fourth condition includes routing a fourth air flow through the exhaust system, the engine, the intake manifold, and the intake, in that order. A second example of the method optionally includes the first example, and further includes wherein the first condition and the third condition includes rotating the engine unfueled via a motor in a forward direction to route the first air flow through the intake, the intake manifold, the engine, and the exhaust system, in that order, and where the second condition and the fourth condition includes rotating the engine unfueled via the motor in a reverse direction to route the second air flow through the exhaust system, the engine, the intake manifold, and the intake, in that order. A third example of the method optionally includes any one or more or each of the first and second examples, and further includes wherein routing the first air flow includes routing the first air flow for a first predetermined duration, and where routing the third air flow includes routing the third air flow for the first predetermined duration; wherein routing the second air flow includes routing the second air flow for a second predetermined duration, where routing the fourth air flow includes routing the fourth air flow for the second predetermined duration, where the first predetermined duration is either the same or different than the second predetermined duration; wherein each of the first condition, second condition, third condition, and fourth condition includes controlling a throttle position in the intake of the vehicle to a predetermined open position; and wherein each of the first condition, second condition, third condition, and fourth condition includes sealing an evaporative emissions system from the intake, intake manifold, engine, and exhaust system, the evaporative emissions system configured to capture and store fuel vapors from a fuel system of the vehicle, and wherein each of the first condition, second condition, third condition, and fourth condition includes sealing the intake, intake manifold, engine, and exhaust system from an exhaust gas recirculation system, the exhaust gas recirculation system configured to route at least a portion of exhaust gases from the engine to the intake manifold. A fourth example of the method optionally includes any one or more or each of the first through third examples, and further comprises indicating the presence of degradation stemming from the intake manifold responsive to the first intake air flow being substantially equivalent to the first baseline intake air flow and where the first exhaust air flow is greater than the first baseline exhaust air flow, and/or where the first intake air flow is substantially equivalent to the first baseline intake air flow and where the second intake air flow is less than the second baseline intake air flow. A fifth example of the method optionally includes any one or more or each of the first through fourth examples, and further comprises indicating the presence of degradation stemming from the exhaust system responsive to the first intake air flow being substantially equivalent to the first baseline intake air flow and where the first exhaust air flow is less than the first baseline exhaust air flow, and/or where the first intake air flow is substantially equivalent to the first baseline intake air flow and where the second intake air flow is greater than the second baseline intake air flow. A sixth example of the method optionally includes any one or more or each of the first through fifth examples, and further comprises indicating the presence of degradation stemming from the engine responsive to the first intake air flow being less than the first baseline intake air flow and responsive to the first exhaust air flow being less than the first baseline exhaust air flow, and/or where the first intake air flow is less than the first baseline intake air flow and where the second intake air flow is less than the second baseline intake air flow. A seventh example of the method optionally includes any one or more or each of the first through sixth examples, and further includes wherein the third condition and the fourth condition are conducted under conditions where degradation in the intake manifold, engine and exhaust system is not already indicated; wherein the first condition, second condition, third condition, and fourth condition are all conducted under conditions where the vehicle is not occupied and where the vehicle is not in motion; and wherein the first intake air flow, the first baseline intake air flow, the second intake air flow, and the second baseline intake air flow are indicated via a mass air flow sensor positioned in the intake manifold of the engine, and where the first exhaust air flow and the first baseline exhaust air flow are indicated via a differential pressure sensor positioned in the exhaust system.

An example of a system for a vehicle comprises an engine system including an intake manifold, an exhaust system, and an engine; a mass air flow sensor positioned in the intake manifold; a motor, capable or rotating the engine unfueled; and a controller, storing instructions in non-transitory memory that, when executed, cause the controller to: obtain a first baseline intake air flow via the mass air flow sensor by rotating the engine unfueled via the motor in a forward direction and obtain a second baseline intake air flow via the mass air flow sensor by rotating the engine unfueled via the motor in a reverse direction, just subsequent to rotating the engine unfueled in the forward direction to obtain the first baseline intake air flow; and responsive to conditions being indicated to be met for conducting an engine system diagnostic to indicate a presence or absence of degradation stemming from the intake manifold, engine, or exhaust system, obtain a first intake air flow via the mass air flow sensor by rotating the engine unfueled via the motor in the forward direction and obtain a second intake air flow via the mass air flow sensor by rotating the engine unfueled via the motor in the reverse direction just subsequent to rotating the engine unfueled in the forward direction to obtain the first intake air flow, and where indicating the presence or absence of degradation involves comparing the first intake air flow to the first baseline intake air flow to yield a first result, comparing the second intake air flow to the second baseline intake air flow to yield a second result, and then comparing the first result to the second result to pinpoint whether degradation is present in the intake manifold, the engine, or the exhaust system. In a first example of the system, the system further includes wherein the controller stores further instructions to indicate degradation stemming from the intake manifold when the first result includes the first intake air flow being substantially equivalent to the first baseline intake air flow, but where the second result includes the second intake air flow being less than the second baseline intake air flow; indicate degradation stemming from the exhaust system when the first result includes the first intake air flow being substantially equivalent to the first baseline intake air flow, but where the second result includes the second intake air flow is greater than the second baseline intake air flow; indicate degradation stemming from the engine when the first result includes the first intake air flow being less than the first baseline intake air flow, and where the second result includes the second intake air flow being less than the second baseline intake air flow; and indicate the absence of degradation stemming from the intake manifold, the engine, or the exhaust system when the first result includes the first intake air flow being substantially equivalent to the first baseline intake air flow, and where the second result includes the second intake air flow being substantially equivalent to the second baseline intake air flow. A second example of the system optionally includes the first example, and further comprises one or more of seat load cells, door sensing technology, and/or onboard cameras, where the seat load cells, door sensing technology and/or onboard cameras are configured to provide information on vehicle operator and passenger occupancy of the vehicle; and wherein the controller stores further instructions to obtain the first baseline intake air flow and the second baseline intake air flow provided there is not already an indication of degradation in the intake manifold, the engine, or the exhaust system; and wherein obtaining the first baseline intake air flow, obtaining the first intake air flow, obtaining the second baseline intake air flow, and obtaining the second intake air flow are conducted under conditions where the vehicle is indicated to be unoccupied.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A system for a vehicle, comprising:
   an engine system including an intake manifold, an exhaust system, and an engine;
   a mass air flow sensor positioned in the intake manifold;
   a motor, capable of rotating the engine unfueled; and
   a controller, storing instructions in non-transitory memory that, when executed, cause the controller to:
   obtain a first baseline intake air flow via the mass air flow sensor by rotating the engine unfueled via the motor in a forward direction and obtain a second baseline intake air flow via the mass air flow sensor by rotating the engine unfueled via the motor in a reverse direction, just subsequent to rotating the engine unfueled in the forward direction to obtain the first baseline intake air flow; and
   responsive to conditions being indicated to be met for conducting an engine system diagnostic to indicate a presence or absence of degradation stemming from the intake manifold, the engine, or the exhaust system, obtain a first intake air flow via the mass air flow sensor by rotating the engine unfueled via the motor in the forward direction and obtain a second intake air flow via the mass air flow sensor by rotating the engine unfueled via the motor in the reverse direction just subsequent to rotating the engine unfueled in the forward direction to obtain the first intake air flow, and where indicating the presence or absence of degradation involves comparing the first intake air flow to the first baseline intake air flow to yield a first result, comparing the second intake air flow to the second baseline intake air flow to yield a second result, and then comparing the first result to the second result to pinpoint whether degradation is present in the intake manifold, the engine, or the exhaust system.

2. The system of claim 1, wherein the controller stores further instructions to indicate degradation stemming from the intake manifold when the first result includes the first intake air flow being substantially equivalent to the first baseline intake air flow, but where the second result includes the second intake air flow being less than the second baseline intake air flow;
   indicate degradation stemming from the exhaust system when the first result includes the first intake air flow being substantially equivalent to the first baseline intake air flow, but where the second result includes the second intake air flow is greater than the second baseline intake air flow;
   indicate degradation stemming from the engine when the first result includes the first intake air flow being less than the first baseline intake air flow, and where the second result includes the second intake air flow being less than the second baseline intake air flow; and
   indicate the absence of degradation stemming from the intake manifold, the engine, or the exhaust system when the first result includes the first intake air flow being substantially equivalent to the first baseline intake air flow, and where the second result includes the second intake air flow being substantially equivalent to the second baseline intake air flow.

3. The system of claim 1, further comprising:

one or more of seat load cells, door sensing technology, and/or onboard cameras, where the seat load cells, door sensing technology and/or onboard cameras are configured to provide information on vehicle operator and passenger occupancy of the vehicle; and wherein the controller stores further instructions to obtain the first baseline intake air flow and the second baseline intake air flow provided there is not already an indication of degradation in the intake manifold, the engine, or the exhaust system; and wherein obtaining the first baseline intake air flow, obtaining the first intake air flow, obtaining the second baseline intake air flow, and obtaining the second intake air flow are conducted under conditions where the vehicle is indicated to be unoccupied.

4. A system for a vehicle, comprising:

an engine including an intake system and an exhaust system;

a mass air flow sensor;

an electric machine; and a controller, storing instructions in non-transitory memory that, when executed, cause the controller to:

indicate a presence or absence of degradation of the intake system or the exhaust system in response to air flows generated via rotating the engine in a first direction and a second direction.

5. The system of claim 4, wherein the engine is rotated in the first direction and the second direction via the electric machine.

6. The system of claim 5, wherein the engine is rotated without supplying fuel to the engine.

7. The system of claim 5, further comprising additional instructions to adjust a position of a throttle to a first position, the engine rotated in the first direction or the second direction while the throttle is in the first position.

8. The system of claim 5, further comprising:

additional instructions to seal an evaporative emissions system.

9. The system of claim 8, where sealing the evaporative emissions system includes closing a purge valve.

10. The system of claim 5, further comprising:

additional instructions to rotate the engine in the first direction at a predetermined speed.

11. The system of claim 5, further comprising:

additional instructions to rotate the engine in the second direction at a predetermined speed.

* * * * *